United States Patent
Ota et al.

(10) Patent No.: US 10,556,036 B2
(45) Date of Patent: Feb. 11, 2020

(54) ABSORBENT ARTICLE INCLUDING HYDROPHOBIZED ADSORBENT

(71) Applicant: LIVEDO CORPORATION, Shikokuchuo-shi, Ehime (JP)

(72) Inventors: Yoshihisa Ota, Mima-gun (JP); Emi Amano, Mima-gun (JP)

(73) Assignee: LIVEDO CORPORATION, Shikokuchuo-shi (JP)

(*) Notice: Subject to any disclaimer, the term of this patent is extended or adjusted under 35 U.S.C. 154(b) by 1058 days.

(21) Appl. No.: 14/417,223

(22) PCT Filed: Jul. 26, 2013

(86) PCT No.: PCT/JP2013/004542
§ 371 (c)(1),
(2) Date: Jan. 26, 2015

(87) PCT Pub. No.: WO2014/017100
PCT Pub. Date: Jan. 30, 2014

(65) Prior Publication Data
US 2015/0246153 A1    Sep. 3, 2015

(30) Foreign Application Priority Data

Jul. 27, 2012   (JP) .................... 2012-167039

(51) Int. Cl.
*A61F 13/15* (2006.01)
*A61F 13/20* (2006.01)
(Continued)

(52) U.S. Cl.
CPC .............. *A61L 15/26* (2013.01); *A61L 15/18* (2013.01); *C08K 9/06* (2013.01)

(58) Field of Classification Search
CPC ....... A61F 13/5323; A61L 15/42; A61L 15/60
See application file for complete search history.

(56) References Cited

U.S. PATENT DOCUMENTS 2,690,415 A  *  9/1954  Shuler ................ A61F 13/8405
                                                                604/365
5,575,785 A      11/1996  Gryskiewicz et al.
(Continued)

FOREIGN PATENT DOCUMENTS

CN       101072871 A      11/2007
CN       102100645 A      6/2011
(Continued)

OTHER PUBLICATIONS

Office Action dated Jun. 21, 2016, issued in counterpart Japanese Patent Application No. 2012-167039, (2 pages).
(Continued)

*Primary Examiner* — Michele M Kidwell
(74) *Attorney, Agent, or Firm* — Westerman, Hattori, Daniels & Adrian, LLP

(57) ABSTRACT

An objective of the present invention is to provide an absorbent article that prevents wetting of the outer sides or surrounding area of the absorbent article due to condensation formed by water vapor escaped from inside the absorbent article. The present invention provides an absorbent article comprising: an absorbent body composed of at least one absorption layer, wherein the absorbent body includes a hydrophobized adsorbent and (a) a water absorbent resin powder having an absorption speed in a range from 6 seconds to 60 seconds determined by a vortex method.

14 Claims, 6 Drawing Sheets

(51) Int. Cl.
    *A61L 15/26* (2006.01)
    *A61L 15/18* (2006.01)
    *C08K 9/06* (2006.01)

(56) References Cited

U.S. PATENT DOCUMENTS

| | | | | |
|---|---|---|---|---|
| 5,649,916 | A * | 7/1997 | DiPalma | A61F 13/534 |
| | | | | 604/365 |
| 6,245,693 | B1 * | 6/2001 | Gagliardi | A61F 13/8405 |
| | | | | 604/359 |
| 6,663,611 | B2 * | 12/2003 | Blaney | A61F 13/51458 |
| | | | | 442/394 |
| 2004/0122386 | A1 * | 6/2004 | Mocadlo | A61L 15/18 |
| | | | | 604/359 |
| 2006/0035352 | A1 | 2/2006 | Payne et al. | |
| 2006/0142709 | A1 * | 6/2006 | Quincy, III | A61L 15/18 |
| | | | | 604/359 |
| 2009/0186542 | A1 | 7/2009 | Kondo et al. | |
| 2010/0036342 | A1 | 2/2010 | Carlucci et al. | |
| 2011/0152364 | A1 | 6/2011 | Bissah et al. | |
| 2012/0219728 | A1 | 8/2012 | Badri et al. | |
| 2013/0102461 | A1 * | 4/2013 | Akiyama | A61F 13/15617 |
| | | | | 502/402 |
| 2013/0206076 | A1 * | 8/2013 | Komatsubara | A01K 1/0107 |
| | | | | 119/171 |
| 2014/0315034 | A1 | 10/2014 | Akiyama et al. | |

FOREIGN PATENT DOCUMENTS

| | | | |
|---|---|---|---|
| CN | 102112082 A | 6/2011 | |
| EP | 1 358 894 A1 | 11/2003 | |
| EP | 1 659 144 * | 5/2006 | ............ C08J 3/12 |
| EP | 2 048 184 A1 | 4/2009 | |
| JP | 56-133028 A | 10/1981 | |
| JP | 2001-046423 A | 2/2001 | |
| JP | 2006-057075 A | 3/2006 | |
| JP | 2008-237430 A | 10/2008 | |
| JP | 2008-247949 A | 10/2008 | |
| JP | 2009-61230 A | 3/2009 | |
| JP | 2010-51654 A | 3/2010 | |
| JP | 2011-182906 A | 9/2011 | |
| JP | 2011-182907 A | 9/2011 | |
| WO | 95/33558 A1 | 12/1995 | |
| WO | 2005/092955 A1 * | 10/2005 | ............ C08J 3/12 |
| WO | 2011/063372 A2 | 5/2011 | |
| WO | 2011/158838 A1 | 12/2011 | |

OTHER PUBLICATIONS

International Search Report dated Sep. 27, 2013, issued in corresponding application No. PCT/JP2013/004542.

Written Opinion of the International Searching Authority dated Sep. 27, 2013, issued in corresponding application No. PCT/JP2013/004542.

Office Action dated Sep. 5, 2016, issued in counterpart Chinese Patent Application No. 201380039904.9, with English translation. (13 pages).

Office Action dated Nov. 25, 2015, issued in counterpart European Patent Application No. 13750955.0 ( 4 pages).

Office Action dated Apr. 22, 2016, issued in counterpart European Patent Application No. 13750955.0 ( 4 pages).

Office Action dated Jan. 24, 2017, issued in counterpart Japanese Patent Application No. 2012-167039, with English translation. (8 pages).

Office Action dated May 16, 2017, issued in counterpart Chinese Patent Application No. 20180039904.9, with English translation. (5 pages).

Notice of Reasons for Rejection dated Jun. 26, 2018, issued in counterpart Japanese Applcation No. 2012-167039, with English translation. (4 pages).

* cited by examiner

[Fig. 1]
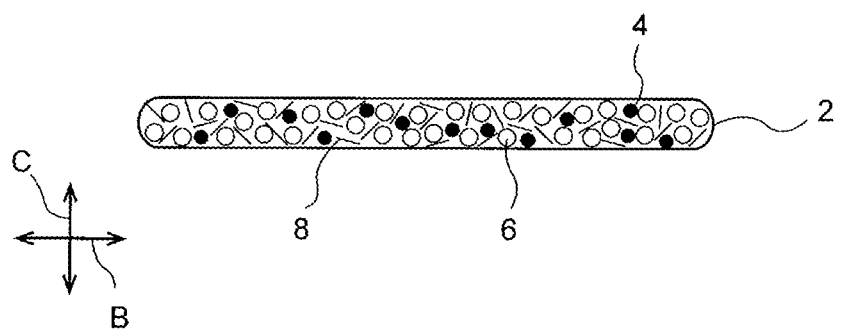
[Fig. 2]
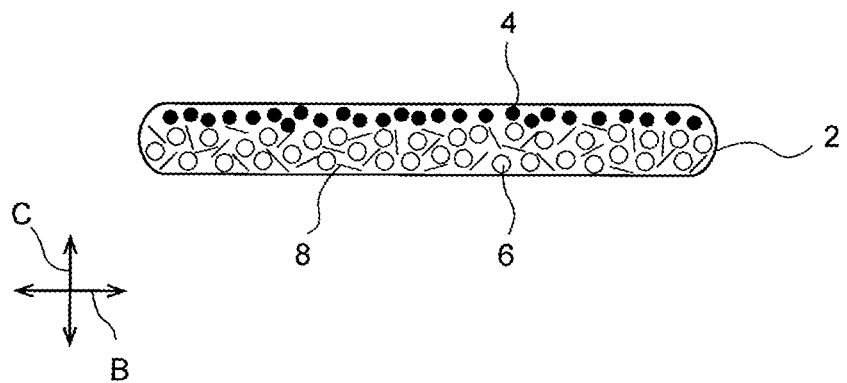

[Fig. 3]
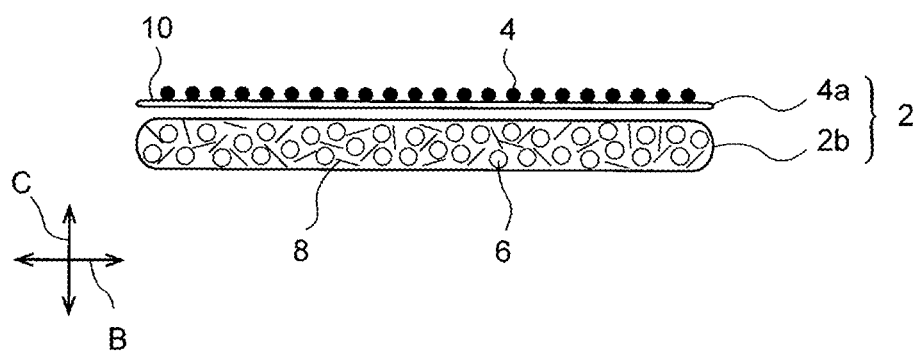
[Fig. 4]
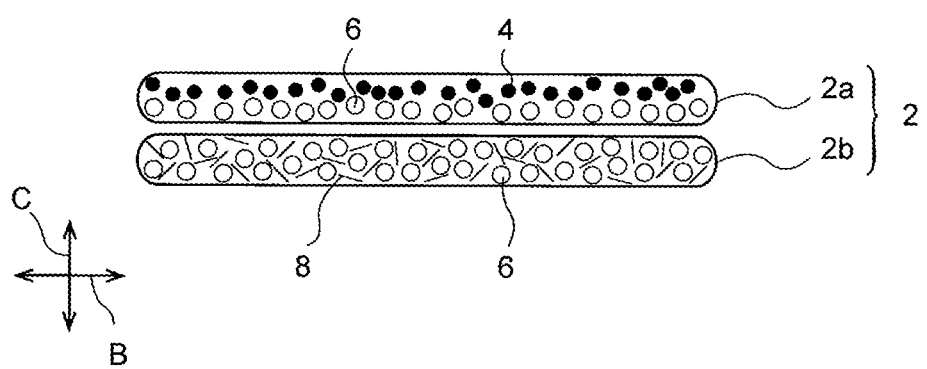

[Fig. 5]
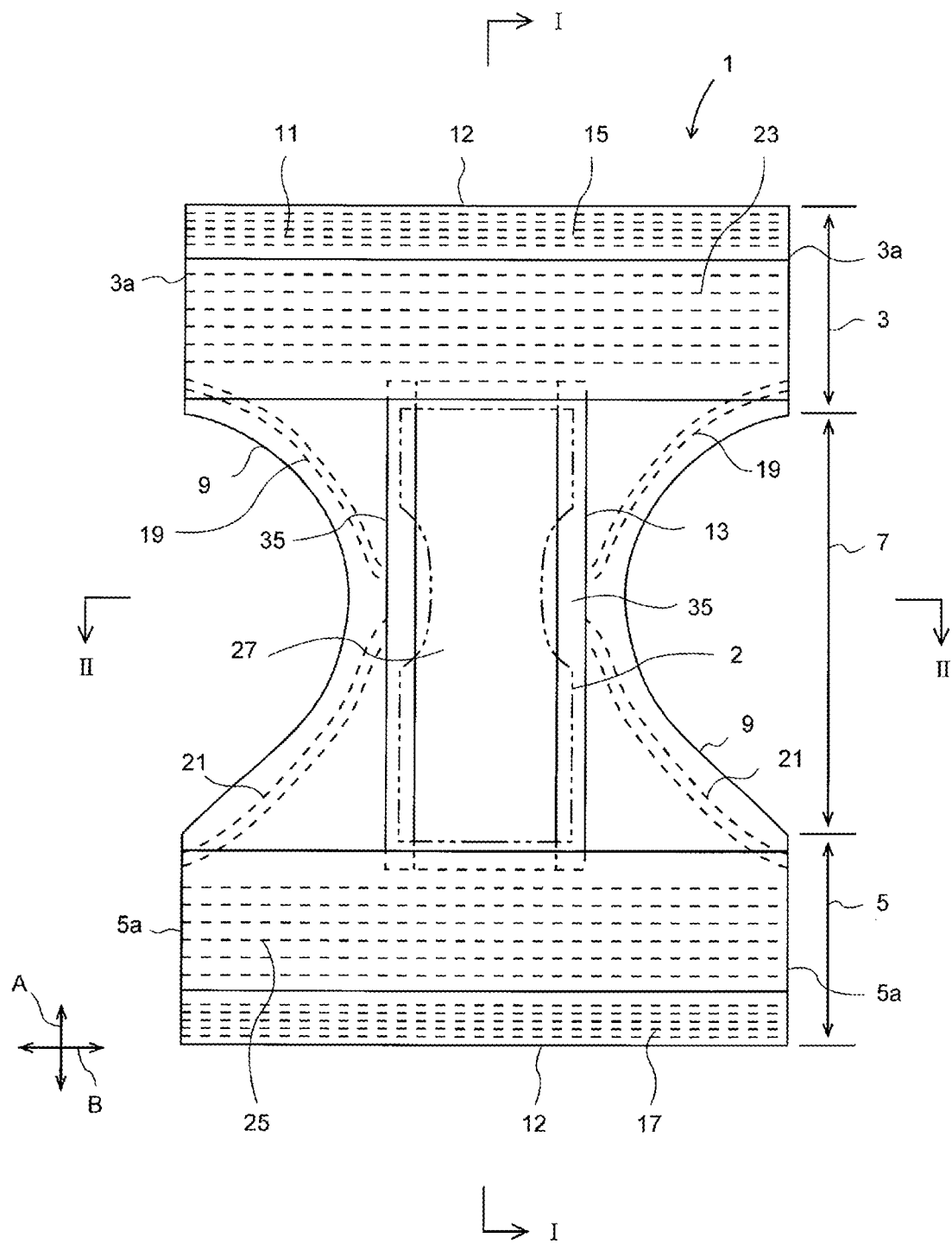

[Fig. 6]
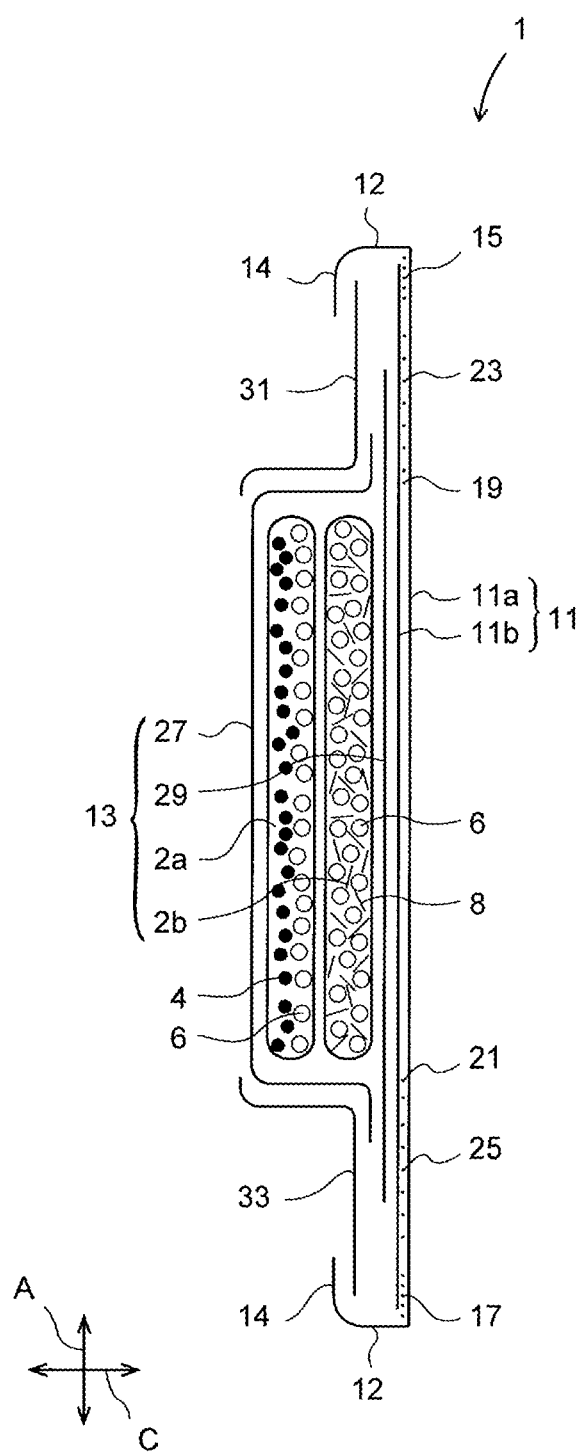

[Fig. 7]
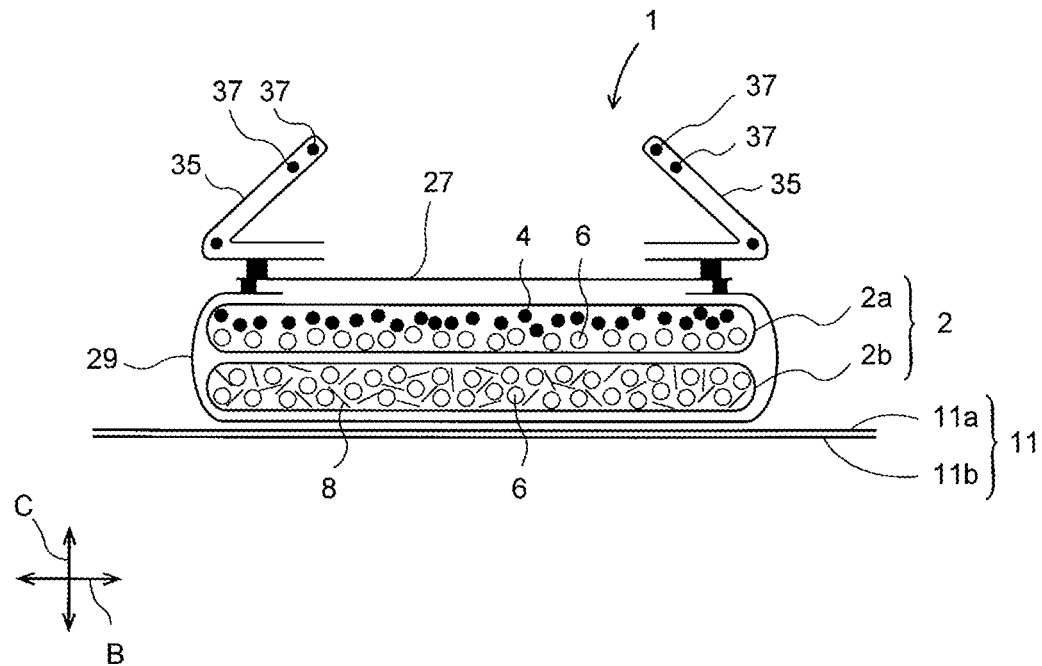
[Fig. 8]
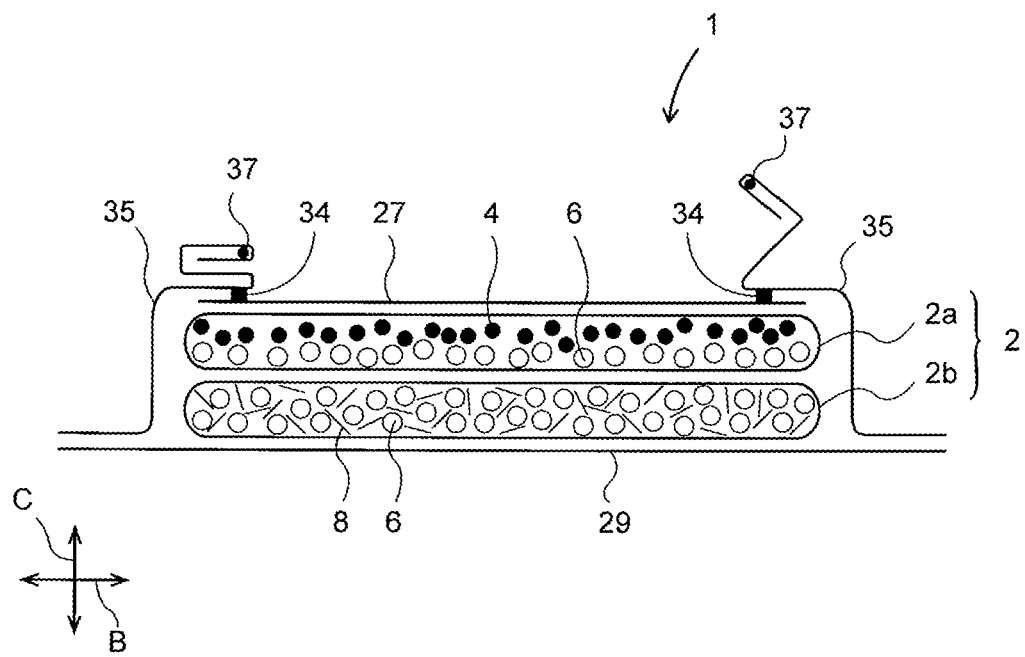

[Fig. 9]
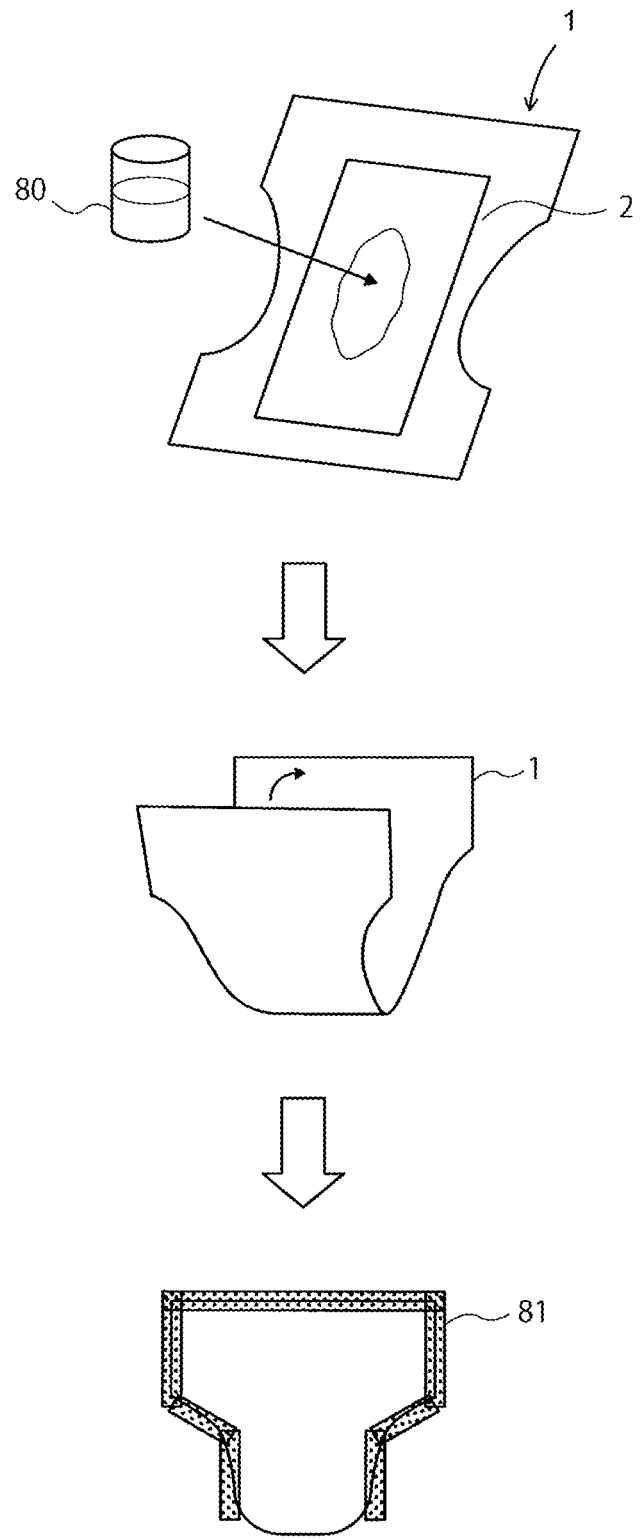

ABSORBENT ARTICLE INCLUDING HYDROPHOBIZED ADSORBENT

TECHNICAL FIELD

The present invention relates to a technique for improving condensation on absorbent articles.

BACKGROUND ART

From a standpoint of preventing dampness and rashes, a moisture permeable sheet is used as an exterior sheet material (back surface material) of absorbent articles such as disposable diapers and sanitary napkins. With an absorbent article using a moisture permeable sheet as a back surface material, there has been a problem that water vapor escaped from inside the absorbent article forms condensation on the outer surface of the absorbent article to wet the worn article or the skin of a wearer who is wearing the absorbent article. In addition, when the wearer's skin or the worn article gets wet due to condensation, it becomes not only unpleasant but also necessary to replace the worn article in some cases.

Absorbent articles that solve the above described problem are disclosed in, for example, Patent Literatures 1 and 2. Patent Literature 1 discloses an absorbent article, which is applied on a region including a crotch portion of a wearer. The absorbent article includes: an absorption core for absorbing moisture; an inner sheet member disposed on a skin surface side of the absorption core and having at least a portion that is water permeable; and an outer sheet member disposed on an external surface side of the absorption core. The outer sheet member includes a porous resin film having breathability and waterproofness, and a water absorbent sheet having breathability and water absorptivity and laminated on an external surface side of the porous resin film.

Patent Literature 2 discloses a urine absorption pad, which is applied on a region including a crotch portion of a wearer. The urine absorption pad includes: an absorption core for absorbing moisture; an inner sheet member disposed on a skin surface side of the absorption core and having at least a portion that is water permeable; and an outer sheet member disposed on an external surface side of the absorption core. The outer sheet includes a porous resin film having breathability and waterproofness, an exterior sheet having breathability and laminated on an external surface side of the porous resin film, and an adhesive mixed with a water absorbent polymer and applied between the porous resin film and the exterior sheet to bond the porous resin film and the exterior sheet.

CITATION LIST

Patent Literature

[PTL 1]
Japanese Patent Publication No. 2011-182906
[PTL 2]
Japanese Patent Publication No. 2011-182907

SUMMARY OF INVENTION

Technical Problem

The present invention has been made in view of the above described circumstances, and an objective of the present invention is to provide an absorbent article that prevents wetting of the outer sides or surrounding area of the absorbent article due to condensation formed by water vapor escaped from inside the absorbent article.

Solution to Problem

In order to prevent the condensation on the absorbent article, it is conceivable to use a physical adsorbent for adsorbing water vapor, in addition to a water absorbent resin powder. However, when body fluid such as urine is excreted to an absorbent body including a water absorbent resin powder and a physical adsorbent for adsorbing water vapor, a problem occurs that the physical adsorbent for adsorbing water vapor absorb the body fluid and thus does not function as an adsorbent for water vapor. As a method for solving such a problem, the gist of the present invention is usage of a water absorbent resin powder having a high absorption speed for body fluid such as urine, and an adsorbent having a low absorption speed for body fluid.

The present invention that has solved the above described problems provides an absorbent article comprising: an absorbent body composed of at least one absorption layer, wherein the absorbent body includes a hydrophobized adsorbent and (a) a water absorbent resin powder having an absorption speed in a range from 6 seconds to 60 seconds determined by a vortex method. That is, the absorbent article of the present invention is provided with an absorbent body including a water absorbent resin powder having a sufficiently high water absorption speed for body fluid, i.e., having an absorption speed in a range from 6 second to 60 seconds determined by the vortex method, and a hydrophobized adsorbent having a low absorption speed for body fluid. By having such a configuration, even when the body fluid is excreted to the absorbent body including the hydrophobized adsorbent and the water absorbent resin powder having an absorption speed in a range from 6 seconds to 60 seconds determined by the vortex method, the water absorbent resin powder immediately absorbs the body fluid before the hydrophobized adsorbent absorbs the body fluid. Therefore, water vapor adsorption performance of the hydrophobized adsorbent does not deteriorate.

Examples of the hydrophobized adsorbent include those obtained by performing a hydrophobization on general adsorbents (e.g., silica, alumina, zeolite, activated carbon). As these hydrophobized adsorbents, for example, at least one selected from the group consisting of hydrophobized silica, hydrophobized alumina, hydrophobized zeolite, and hydrophobized activated carbon can be preferably used.

The water absorbent resin powder preferably satisfies the following requirements of (b) to (d).
(b) Moisture absorption blocking rate: 10% or lower
(c) Absorption ratio: 30 g/g to 70 g/g
(d) Water retention amount: 25 g/g to 65 g/g
If the water absorbent resin powder satisfies the above described (b) to (d), reversal and leakage of excreted body fluid can be further suppressed.

The absorbent body preferably includes the hydrophobized adsorbent in an amount from 0.01 part by mass to 20 parts by mass with respect to 100 parts by mass of the water absorbent resin powder. In addition, the absorbent body preferably includes the hydrophobized adsorbent on a skin surface side thereof, since water vapor adsorption performance of the absorbent body becomes enhanced.

The absorbent article of the present invention preferably comprises a surface sheet material disposed on a skin surface side of the absorbent body and a liquid impermeable exterior sheet material disposed on an external surface side of the absorbent body, wherein at least one part of the surface sheet material is liquid permeable. The absorbent article of the present invention is suitable as, for example, open-type or pants-type disposable diapers.

Advantageous Effects of Invention

According to the present invention, it is possible to suppress the condensation of water vapor on the outer side of the absorbent article.

BRIEF DESCRIPTION OF DRAWINGS

FIG. 1 is a schematic sectional view showing one example of an absorbent body of an absorbent article of the present invention.

FIG. 2 is a schematic sectional view showing one example of the absorbent body of the absorbent article of the present invention.

FIG. 3 is a schematic sectional view showing one example of the absorbent body of the absorbent article of the present invention.

FIG. 4 is a schematic sectional view showing one example of the absorbent body of the absorbent article of the present invention.

FIG. 5 is a plan view (expansion plan) of one example of the absorbent article of the present invention.

FIG. 6 is a schematic sectional view along line I-I in FIG. 5.

FIG. 7 is a schematic sectional view along line II-II in FIG. 5.

FIG. 8 is a schematic sectional view of another example of the absorbent article of the present invention.

FIG. 9 is a schematic view showing the absorbent article in a sealed state for the human test.

DESCRIPTION OF EMBODIMENTS

The present invention is directed to an absorbent article comprising: an absorbent body composed of at least one absorption layer, wherein the absorbent body includes a hydrophobized adsorbent and (a) a water absorbent resin powder having an absorption speed in a range from 6 seconds to 60 seconds determined by a vortex method.

Water Absorbent Resin Powder

First, a water absorbent resin powder for use in the present invention will be described. As described above, in the present invention, a water absorbent resin powder having a high absorption speed for body fluid is used. From this standpoint, the water absorbent resin powder used in the present invention has (a) an absorption speed in a range from 6 seconds to 60 seconds determined by the vortex method. The absorption speed of the water absorbent resin powder determined by the vortex method is preferably 6 seconds or more and more preferably 10 seconds or more, and is preferably 58 seconds or less, and more preferably 55 seconds or less. If the absorption speed is above 60 seconds, body fluid cannot be sufficiently absorbed when a large amount of the body fluid is excreted at a high speed at once. As a result, leakage of liquid may occur easily. In addition, there may be cases where the hydrophobized adsorbent absorbs the body fluid. The absorption speed is more preferred if it is smaller, but if the absorption speed is less than 6 seconds, the stability of the water absorbent resin powder against urine, in particular, the stability to urine under a load may deteriorate. The absorption speed determined by the vortex method is evaluated by measuring time (seconds) required for absorbing body fluid. Therefore, the smaller measuring time (seconds) means the higher speed to absorb body fluid by the water-absorbent resin powder.

The water-absorbent resin powder has (d) a moisture absorption blocking ratio of 10% or less. The moisture absorption blocking ratio is more preferably 8% or less, and even more preferably 5% or less. If the moisture absorption blocking ratio is 10% or less, the aggregation of the water-absorbent resin powder is suppressed. Thus, when an absorber is manufactured, the water-absorbent resin powder is unlikely to be stuck in a feed pipe in a manufacturing machine or a manufacturing line, or the water-absorbent resin powder is able to be uniformly applied to a nonwoven fabric. In addition, reversal of the excreted body fluid can be further suppressed.

The water-absorbent resin powder of the present invention preferably has an absorption ratio of 30 g/g or more and preferably has an absorption ratio of 70 g/g or less. The water-absorbent resin powder of the present invention preferably has an absorption ratio of 35 g/g or more, more preferably 40 g/g or more, and preferably has an absorption ratio of 68 g/g or less, more preferably 66 g/g or less. The absorption ratio is a measure indicating how much water the water-absorbent resin powder can absorb. If the absorption ratio is 30 g/g or more, a small amount of the water-absorbent resin powder can maintain an absorption capacity at a predetermined level, and thus it is easy to manufacture a thin absorber. In light of prevention of liquid leakage, the absorption ratio is more preferred if it is greater, but the absorption ratio is more preferably 70 g/g or less. This is because if the absorption ratio is 70 g/g or less, the stability of the water-absorbent resin powder to urine is improved.

The water-absorbent resin powder preferably has a water retention amount of 25 g/g or more, and preferably has a water retention amount of 65 g/g or less. The water-absorbent resin powder preferably has a water retention amount of 26 g/g or more, more preferably 27 g/g or more, and preferably has a water retention amount of 63 g/g or less, more preferably 60 g/g or less. The water retention amount is a measure indicating how much absorbed liquid the water-absorbent resin powder can retain. If the water retention amount is 25 g/g or more, a small amount of the water-absorbent resin powder can maintain a body fluid-retaining capacity at a predetermined level, and thus it is easy to manufacture a thin absorber. In light of prevention of liquid leakage, the water retention amount is more preferred if it is greater, but the water retention amount is more preferably 65 g/g or less. This is because if the water retention amount is 65 g/g or less, the stability of the water-absorbent resin powder to urine is improved.

Although there is no particular limitation on (e) a liquid-passing speed under a load of the water absorbent resin powder, the liquid-passing speed under a load is preferably 1200 seconds or less. The liquid-passing speed under a load is more preferably 800 seconds or less, even more preferably 400 seconds or less, and particularly preferably 100 seconds or less. If the liquid-passing speed under a load is 1200 seconds or less, the diffusion of the body fluid inside the absorbent body is unlikely to deteriorate. Therefore, leakage of liquid is further suppressed. The liquid-passing speed under a load is evaluated by measuring the time (seconds) required for a certain amount of liquid to pass through a water absorbent resin powder that has absorbed water in advance to be swollen and to which a load is applied. Therefore, the smaller measuring time (seconds) means the higher liquid-passing speed. It should be noted that the lower limit of the liquid-passing speed is not particularly limited, and is ordinarily about 1 second.

The absorption speed, moisture absorption blocking rate, absorption ratio, water retention amount, and liquid-passing speed under a load of the water absorbent resin powder can be adjusted by appropriately selecting a composition of a later described crosslinked polymer (A), the type of a surface modifier, the particle size of the water absorbent resin powder, and the drying condition, etc.

Any water absorbent resin powder can be used in the present invention, as long as the water absorbent resin powder has an absorption speed in a range from 6 seconds to 60 seconds determined by a vortex method. Preferably used is a crosslinked polymer (A) mainly composed of acrylic acid and having carboxyl groups thereof being at least partially neutralized. The content of an acrylic acid component forming the crosslinked polymer (A) is preferably 90 mass % or more, and more preferably 95 mass % or more, and is preferably 99 mass % or less and more preferably 97 mass % or less. If the content of the acrylic acid component is within the above described range, the obtained water absorbent resin powder can easily exhibit a desired absorption performance.

Examples of cations for neutralizing at least a part of the carboxyl groups of the crosslinked polymer (A) include, but not particularly limited to, alkali metal ions such as lithium, sodium, and potassium, and alkaline earth metal ions such as magnesium and calcium. Of those described above, at least a part of the carboxyl groups of the crosslinked polymer is preferably neutralized with the sodium ion. It should be noted that, with regard to neutralization of the carboxyl groups of the crosslinked polymer, neutralization may be conducted on the carboxyl groups of the crosslinked polymer which has been obtained by polymerization (preferably neutralization may be conducted while chopping a water-containing gel composed of the crosslinked polymer and water) or neutralization may be conducted in advance on a monomer which is then used for forming the crosslinked polymer.

The degree of neutralization of the carboxyl groups of the crosslinked polymer is preferably 60 mole % or more, and more preferably 65 mole % or more. This is because there are cases where the absorption performance of the obtained water-absorbent resin powder deteriorates if the degree of neutralization is too low. Furthermore, there is no particular limitation on the upper limit of the degree of neutralization, and all the carboxyl groups may be neutralized. It should be noted that the degree of neutralization is obtained by the following formula.

Degree of neutralization (mole %)=100×[Number of moles of neutralized carboxyl groups in the crosslinked polymer]/[Total number of moles of the carboxyl groups in the crosslinked polymer (including neutralized and unneutralized groups)]

The crosslinked polymer (A) preferably includes those obtained by polymerization of the unsaturated monomer composition containing a water-soluble ethylenically unsaturated monomer (a1)) and/or a hydrolyzable monomer (a2) producing the water-soluble ethylenically unsaturated monomer (a1)) by hydrolysis and an internal crosslinking agent (b).

The water-soluble ethylenically unsaturated monomer (a1)) is not particularly limited, but a monomer having at least one water-soluble substituent and an ethylenically unsaturated group, or the like can be used. The water-soluble monomer means a monomer having a property of being dissolved in an amount of at least 100 g in 100 g of water at 25 degrees centigrade. In addition, the hydrolyzable monomer (a2) is hydrolyzed with water at 50 degrees centigrade, by the action of a catalyst (an acid, a base, or the like) where necessary, to produce the water-soluble ethylenically unsaturated monomer (a1). The hydrolysis of the hydrolyzable monomer (a2) may be conducted during or after the polymerization of the crosslinked polymer (A) or both during and after the polymerization of the crosslinked polymer (A). However, the hydrolysis of the hydrolyzable monomer (a2) is preferably conducted after the polymerization of the crosslinked polymer (A) in light of the molecular weight of the obtained water-absorbent resin powder and the like.

Examples of the water-soluble substituent include a carboxyl group, a sulfo group, a sulfoxy group, a phosphono group, a hydroxyl group, a carbamoyl group, an amino group, or salts thereof and an ammonium salt. A salt of a carboxyl group (a carboxylate), a salt of a sulfo group (a sulfonate), and an ammonium salt are preferred. In addition, examples of the salts include salts of alkali metal such as lithium, sodium, and potassium and salts of alkaline earth metal such as magnesium and calcium. The ammonium salt may be any of salts of primary to tertiary amines or a quaternary ammonium salt. Of these salts, in light of absorption properties, alkali metal salts and ammonium salts are preferred, and alkali metal salts are more preferred, and sodium salts are further preferred.

As the water-soluble ethylenically unsaturated monomer having a carboxyl group and/or a salt thereof, an unsaturated carboxylic acid having 3 to 30 carbon atoms and/or a salt thereof are preferred. Specific examples of the water-soluble ethylenically unsaturated monomer having a carboxyl group and/or a salt thereof include unsaturated monocarboxylic acids and/or salts thereof such as (meth)acrylic acid, (meth)acrylic acid salt, crotonic acid, and cinnamic acid; unsaturated dicarboxylic acids and/or salts thereof such as maleic acid, maleate, fumaric acid, citraconic acid, and itaconic acid; and monoalkyl (1 to 8 carbon atoms) esters of unsaturated dicarboxylic acids and/or salts thereof such as maleic acid monobutyl ester, fumaric acid monobutyl ester, ethylcarbitol monoester of maleic acid, ethylcarbitol monoester of fumaric acid, citraconic acid monobutyl ester, and itaconic acid glycol monoester. It is noted that in the description of the present invention, "(meth)acrylic" means "acrylic" and/or "methacrylic".

As a water-soluble ethylenically unsaturated monomer having a sulfo group and/or a salt thereof, a sulfonic acid having 2 to 30 carbon atoms and/or a slat thereof are preferred. Specific examples of the water-soluble ethylenically unsaturated monomer having a sulfo group and/or a salt thereof include aliphatic or aromatic vinyl sulfonic acids such as vinyl sulfonic acid, (meth)allyl sulfonic acid, styrene sulfonic acid, and alpha-methyl styrene sulfonic acid; (meth)acryloyl-containing alkyl sulfonic acids such as (meth)acryloxy propyl sulfonic acid, 2-hydroxy-3-(meth)acryloxy propyl sulfonic acid, 2-(meth)acryloylamino-2,2-dimethylethane sulfonic acid, 3-(meth)acryloxyethane sulfonic acid, 2-meth(acrylamide-2-methylpropane sulfonic acid, and 3-(meth)acrylamide-2-hydroxypropane sulfonic acid; and alkyl(meth)allyl sulfosuccinate.

Examples of a water-soluble ethylenically unsaturated monomer having a sulfoxy group and/or a salt thereof include sulfate ester of hydroxyalkyl (meth)acrylate; and sulfate ester of polyoxyalkylene mono(meth)acrylate.

Examples of a water-soluble ethylenically unsaturated monomer having a phosphono group and/or a salt thereof include phosphate monoesters of (meth)acrylic acid hydroxyalkyl, phosphate diesters of (meth)acrylic acid hydroxyalkyl, and (meth)acrylic acid alkylphosphonic acids.

Examples of a water-soluble ethylenically unsaturated monomer having a hydroxyl group include mono-ethylenically unsaturated alcohols having 3 to 15 carbon atoms such as (meth)allyl alcohol and (meth)propenyl alcohol; mono-ethylenically unsaturated carboxylates or mono-ethylenically unsaturated ethers of bivalent to hexavalent polyols such as alkylene glycol having 2 to 20 carbon atoms, glycerin, sorbitan, diglycerin, pentaerythritol, and polyalkylene (2 to 4 carbon atoms) glycol (weight average molecular weight: 100 to 2000). Specific examples of them include hydroxyethyl(meth)acrylate, hydroxypropyl(meth)acrylate, triethyleneglycol(meth)acrylate, and poly-oxyethylene-oxy-propylene mono(meth)allyl ether.

Examples of a water-soluble ethylenically unsaturated monomer having a carbamoyl group include (meth)acrylamide; N-alkyl (1 to 8 carbon atoms) (meth)acrylamides such as N-methyl acrylamide; N,N-dialkyl (alkyl having 1 to 8 carbon atoms) acrylamides such as N,N-dimethyl acrylamide and N,N-di-n- or i-propyl acrylamide; N-hydroxyalkyl (1 to 8 carbon atoms) (meth)acrylamides such as N-methylol (meth)acrylamide and N-hydroxyethyl (meth)acrylamide; and N,N-dihydroxyalkyl (1 to 8 carbon atoms) (meth)acrylamides such as N,N-dihydroxyethyl (meth)acrylamide. As an unsaturated monomer having a group composed of an amide, in addition to them, vinyl lactams having 5 to 10 carbon atoms (N-vinyl pyrrolidone, etc.) and the like can also be used.

Examples of a water-soluble ethylenically unsaturated monomer having an amino group include an amino group-containing ester of a mono-ethylenically unsaturated mono- or di-carboxylic acid and an amino group-containing amide of a mono-ethylenically unsaturated mono- or di-carboxylic acid. As the amino group-containing ester of a mono-ethylenically unsaturated mono- or di-carboxylic acid, dialkylaminoalkyl(meth)acrylate, di(hydroxyalkyl)aminoalkyl ester, morpholinoalkyl ester, and the like can be used, and examples thereof include dimethylaminoethyl (meth)acrylate, diethylamino (meth)acrylate, morpholinoethyl (meth)acrylate, dimethylaminoethyl fumarate, and dimethylaminoethyl malate. As the amino group-containing amide of a mono-ethylenically unsaturated mono- or di-carboxylic acid, monoalkyl (meth)acrylamide is preferred, and examples thereof include dimethylaminoethyl (meth)acrylamide and diethylaminoethyl (meth)acrylamide. As the water-soluble ethylenically unsaturated monomer having an amino group, in addition to them, vinylpyridines such as 4-vinylpyridine and 2-vinylpyridine can also be used.

The hydrolyzable monomer (a2) producing the water-soluble ethylenically unsaturated monomer (a1)) by hydrolysis is not particularly limited, but an ethylenically unsaturated monomer having at least one hydrolyzable substituent that becomes a water-soluble substituent by hydrolysis is preferred. Examples of the hydrolyzable substituent include a group containing an acid anhydride, a group containing an ester linkage, and a cyano group.

As an ethylenically unsaturated monomer having a group containing an acid anhydride, an unsaturated dicarboxylic anhydride having 4 to 20 carbon atoms is used, and examples thereof include maleic anhydride, itaconic anhydride, and citraconic anhydride. Examples of an ethylenically unsaturated monomer having a group containing an ester linkage include lower alkyl esters of mono-ethylenically unsaturated carboxylic acids such as methyl (meth)acrylate and ethyl (meth)acrylate; and esters of mono-ethylenically unsaturated alcohols such as vinyl acetate and (meth)allyl acetate. Examples of an ethylenically unsaturated monomer having a cyano group include vinyl group-containing nitrile compounds having 3 to 6 carbon atoms such as (meth)acrylonitrile and 5-hexenenitrile.

As the water-soluble ethylenically unsaturated monomer (a1)) and the hydrolyzable monomer (a2), those described in Japanese Patent No. 3648553, Japanese Patent Publication No. 2003-165883, Japanese Patent Publication No. 2005-75982, and Japanese Patent Publication No. 2005-95759 can be further used.

As each of the water-soluble ethylenically unsaturated monomer (a1) and the hydrolyzable monomer (a2), a single monomer or a mixture of two or more monomers may be used. The same applies to the case where the water-soluble ethylenically unsaturated monomer (a1) and the hydrolyzable monomer (a2) are used in combination. In addition, when the water-soluble ethylenically unsaturated monomer (a1) and the hydrolyzable monomer (a2) are used in combination, the molar content ratio (a1/a2) of them is preferably from 75/25 to 99/1, more preferably from 85/15 to 95/5, even more preferably from 90/10 to 93/7, and most preferably from 91/9 to 92/8. When the molar content ratio falls within the above range, the absorbing performance becomes further preferable.

As the monomer constituting the crosslinked polymer (A), in addition to the water-soluble ethylenically unsaturated monomer (a1)) and the hydrolyzable monomer (a2), another vinyl monomer (a3) that is copolymerizable with these monomers can be used. As the copolymerizable other vinyl monomer (a3), hydrophobic vinyl monomers and the like can be used, but it is not limited to them. As the other vinyl monomer (a3), the following vinyl monomers (i) to (iii) and the like are used.

(i) Aromatic ethylenically unsaturated monomers having 8 to 30 carbon atoms;

Styrenes such as styrene, alpha-methylstyrene, vinyltoluene, and hydroxystyrene; vinylnaphthalene; and halogen substitutions of styrene such as dichlorostyrene.

(ii) Aliphatic ethylenically unsaturated monomers having 2 to 20 carbon atoms;

Alkenes such as ethylene, propylene, butene, isobutylene, pentene, heptene, diisobutylene, octene, dodecene, and octadecene; and alkadienes such as butadiene, and isoprene.

(iii) Alicyclic ethylenically unsaturated monomers having 5 to 15 carbon atoms;

Mono-ethylenically unsaturated monomers such as pinene, limonene, and indene; and polyethylenic vinyl-polymerizable monomers such as cyclopentadiene, bicyclopentadiene, and ethylidene norbornene.

As the other vinyl monomer (a3), those described in Japanese Patent No. 3648553, Japanese Publication No. 2003-165883, Japanese Patent Publication No. 2005-75982, and Japanese Patent Publication No. 2005-95759 can be further used.

When the other vinyl monomer (a3) is used, the content (mole %) of the other vinyl monomer (a3) with respect to the total amount (100 mole %) of the water-soluble ethylenically unsaturated monomer (a1)) and the hydrolyzable monomer (a2) is preferably 0.01 mole % to 5 mole %, more preferably 0.05 mole % to 3 mole %, even more preferably 0.08 mole % to 2 mole %, and most preferably 0.1 mole % to 1.5 mole %. It is noted that in light of absorption properties, the content of the other vinyl monomer (a3) is most preferably 0 mole %.

Examples of the internal crosslinking agent (b) can include an internal crosslinking agent (b1) having two or more ethylenically unsaturated groups, an internal crosslinking agent (b2) having: at least one functional group that can react with a water-soluble substituent of the water-soluble ethylenically unsaturated monomer (a1)) and/or a water-soluble substituent produced by hydrolysis of the hydrolyzable monomer (a2); and at least one ethylenically unsaturated group, and an internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2).

Examples of the internal crosslinking agent (b1) having two or more ethylenically unsaturated groups include bis (meth)acrylamides having 8 to 12 carbon atoms, poly(meth) acrylates of polyols having 2 to 10 carbon atoms, polyallylamines having 2 to 10 carbon atoms, and poly(meth)allyl ethers of polyols having 2 to 10 carbon atoms. Specific examples of them include N,N'-methylene bis(meth)acrylamide, ethylene glycol di(meth)acrylate, poly (polymerization degree of 2 to 5) ethylene glycol di(meth)acrylate, propylene glycol di(meth)acrylate, glycerol (di or tri)acrylate, trimethylol propane triacrylate, diallylamine, triallylamine, triallylcyanurate, triallylisocyanurate, tetraallyloxyethane, pentaerythritol diallyl ether, pentaerythritol triallyl ether, pentaerythritol tetraallyl ether, and diglycerin di(meth) acrylate.

Examples of the internal crosslinking agent (b2) having at least one functional group that can react with a water-soluble substituent of the water-soluble ethylenically unsaturated monomer (a1) and/or a water-soluble substituent produced by hydrolysis of the hydrolyzable monomer (a2) and at least one ethylenically unsaturated group include ethylenically unsaturated compounds having 6 to 8 carbon atoms and an epoxy group, ethylenically unsaturated compounds having 4 to 8 carbon atoms and a hydroxyl group, and ethylenically unsaturated compounds having 4 to 8 carbon atoms and an isocyanato group. Specific examples of them include glycidyl (meth)acrylate, N-methylol (meth)acrylamide, hydroxyethyl (meth)acrylate, and isocyanato ethyl (meth) acrylate.

Examples of the internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2) can include polyhydric alcohols, polyvalent glycidyls, polyvalent amines, polyvalent aziridines, and polyvalent isocyanates. Examples of polyvalent glycidyl compounds include ethylene glycol diglycidyl ether and glycerin diglycidyl ether. Examples of polyvalent amine compounds include ethylenediamine, diethylenetriamine, triethylenetetramine, tetraethylenepentamine, pentaethylenehexamine, and polyethyleneimine. Examples of polyvalent aziridine compounds include Chemitite PZ-33 {2,2-bishydroxymethylbutanol-tris(3-(1-aziridinyl)propionate)}, Chemitite HZ-22 {1,6-hexamethylenediethyleneurea}, and Chemitite DZ-22 {diphenylmethane-bis-4,4'-N,N'-diethyleneurea}, available from Nippon Shokubai Co., Ltd. Examples of polyvalent polyisocyanate compounds include 2,4-tolylene diisocyanate and hexamethylene diisocyanate. These internal crosslinking agents may be used singly or two or more of them may be used in combination.

As the internal crosslinking agent (b), in light of absorbing performance (in particular, an absorption amount, an absorption speed, etc.), the internal crosslinking agent (b1) having two or more ethylenically unsaturated groups is preferred, poly(meth)allyl ethers of polyols having 2 to 10 carbon atoms are more preferred, triallylcyanurate, triallylisocyanurate, tetraallyloxyethane, or pentaerythritol triallyl ether is further preferred, and pentaerythritol triallyl ether is most preferred.

As the internal crosslinking agent (b), those described in Japanese Patent No. 3648553, Japanese Patent Publication No. 2003-165883, Japanese Patent Publication No. 2005-75982, and Japanese Patent Publication No. 2005-95759 can be further used.

The content (mole %) of the internal crosslinking agent (b) with respect to the total amount (100 mole %) of the water-soluble ethylenically unsaturated monomer (a1)) and the hydrolyzable monomer (a2) is preferably from 0.001 mole % to 5 mole %, more preferably from 0.005 mole % to 3 mole %, and even more preferably from 0.01 mole % to 1 mole %. When the content falls within this range, the absorbing performance (in particular, an absorption amount, an absorption speed, etc.) becomes further favorable.

As the method for polymerizing the crosslinked polymer (A), a conventionally known method and the like can be used, and a solution polymerization method, an emulsion polymerization method, a suspension polymerization method, and a reversed-phase suspension polymerization method can be used. In addition, a polymerization liquid at the polymerization may be in the form of a thin film, mist, or the like. As the method for controlling the polymerization, an adiabatic polymerization method, a temperature-controlled polymerization method, an isothermal polymerization method, and the like can be used.

When the suspension polymerization method or the reversed-phase suspension polymerization method is employed as the polymerization method, conventionally known dispersants such as sucrose esters, phosphates, and sorbitan esters, protective colloids such as poval, alpha-olefin-maleic anhydride copolymers, and oxidized polyethylene, and the like can be used where necessary. In addition, in the case with the reversed-phase suspension polymerization method, polymerization can be conducted by using a solvent such as cyclohexane, normal hexane, normal heptane, toluene, and xylene. As the polymerization method, the solution polymerization method is preferred, and an aqueous solution polymerization method is more preferred since an organic solvent and the like are not used and it is advantageous in terms of production cost.

A water-containing gel {consisting of the crosslinked polymer and water} obtained by the polymerization can be chopped where necessary. The size (largest diameter) of the chopped gel is preferably from 50 micrometers to 10 cm, more preferably from 100 micrometers to 2 cm, and even more preferably from 1 mm to 1 cm. If the size falls within this range, dryability during a drying process becomes further favorable.

The chopping can be conducted by a known method, and can be conducted, for example, by using a conventional chopping apparatus such as a Bexmill, a rubber chopper, a Pharma Mill, a mincing machine, an impact type mill, and a roll type mill.

When a solvent (an organic solvent, water, etc.) is used for the polymerization, it is preferred to remove the solvent by distillation after the polymerization. When the solvent contains an organic solvent, the content (mass %) of the organic solvent with respect to the mass (100 mass %) of the crosslinked polymer after the removal by distillation is preferably from 0 mass % to 10 mass %, more preferably from 0 mass % to 5 mass %, even more preferably from 0 mass % to 3 mass %, and most preferably from 0 mass % to 1 mass %. When the content of the organic solvent falls within the above range, the absorbing performance (in particular, water retention amount) of the water-absorbent resin powder becomes further favorable.

When the solvent contains water, the water content (mass %) with respect to the mass (100 mass %) of the crosslinked polymer after the removal by distillation is preferably from 0 mass % to 20 mass %, more preferably from 1 mass % to 10 mass %, even more preferably from 2 mass % to 9 mass %, and most preferably from 3 mass % to 8 mass %. When the water content (% by mass) falls within the above range, the absorbing performance and the breakability of the water-absorbent resin powder after drying become further favorable.

It is noted that the content of the organic solvent and the water content are obtained based on a decrease in the mass of a measurement sample from before heating to after heating by an infrared moisture measuring instrument {JE400 manufactured by Kett Electric Laboratory or the like: 120 plus or minus 5 degrees centigrade, 30 minutes, an atmospheric humidity before heating of 50 plus or minus 10% RH, lamp specifications of 100 V and 40 W}.

As the method for removing the solvent (including water) by distillation, a method in which removal by distillation (drying) is conducted by hot air at a temperature in a range from 80 degrees centigrade to 230 degrees centigrade, a thin film drying method with a drum dryer or the like heated at the temperature in a range from 100 degrees centigrade to 230 degrees centigrade, a (heating) reduced-pressure drying method, a freeze-drying method, a drying method with infrared rays, decantation, filtration, and the like can be used.

The crosslinked polymer (A) can be pulverized after being dried. The pulverizing method is not particularly limited, and, for example, an ordinary pulverizing apparatus such as a hammer type pulverizer, an impact type pulverizer, a roll type pulverizer, and a jet streaming type pulverizer can be used. The particle size of the pulverized crosslinked polymer (A) can be adjusted by sieving or the like where necessary.

The weight average particle size (micrometer) of the crosslinked polymer (A) that is sieved where necessary is preferably from 100 micrometers to 800 micrometers, more preferably from 200 micrometers to 700 micrometers, even more preferably from 250 micrometers to 600 micrometers, particularly preferably from 300 micrometers to 500 micrometers, and most preferably from 350 micrometers to 450 micrometers. When the weight average particle size (micrometer) of the crosslinked polymer (A) falls within the above range, the absorbing performance becomes further favorable.

It is noted that the weight average particle size is measured with a ro-tap test sieve shaker and standard sieves (JIS Z8801-1: 2006) according to the method described in Perry's Chemical Engineers Handbook, Sixth Edition (The McGraw-Hill Companies, 1984, Page 21). In other words, as JIS standard sieves, for example, sieves of 1000 micrometers, 850 micrometers, 710 micrometers, 500 micrometers, 425 micrometers, 355 micrometers, 250 micrometers, 150 micrometers, 125 micrometers, 75 micrometers, and 45 micrometers, and a tray are combined in order from above. About 50 g of a measurement particle is placed into the uppermost sieve, and shaken with the ro-tap test sieve shaker for 5 minutes. The weights of the measurement particles on each sieve and the tray are measured, and the weight fraction of the particles on each sieve is obtained with the total weight regarded as 100% by weight. The values are plotted in a log probability paper {the horizontal axis is used for the opening of the sieve (particle size) and the vertical axis is used for the weight fraction}, then a line is drawn so as to connect each point, and a particle size corresponding to 50% by mass of the mass fraction is obtained and regarded as a weight average particle size.

In addition, the lower the content of fine particles is, the more favorable the absorbing performance becomes. Thus, the content of fine particles having a size of 106 micrometers or less (preferably, 150 micrometers or less) in the entire particles is preferably 3 mass % or less, and even more preferably 1 mass % or less. The content of fine particles can be obtained by using the plot created when the above weight average particle size is obtained.

The crosslinked polymer (A) can be subjected to surface crosslinking where necessary. As a crosslinking agent for conducting the surface crosslinking (a surface crosslinking agent), the same ones as the internal crosslinking agent (b) can be used. In light of absorption performance and the like of the water-absorbent resin powder, the surface crosslinking agent is preferably the crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2), more preferably a polyvalent glycidyl, even more preferably ethylene glycol diglycidyl ether and glycerin diglycidyl ether, and most preferably ethylene glycol diglycidyl ether.

In the case of conducting the surface crosslinking, the content (mass %) of the surface crosslinking agent with respect to the total mass (100 mass %) of the water-soluble ethylenically unsaturated monomer (a1) and/or the hydrolyzable monomer (a2), the internal crosslinking agent (b), and the other vinyl monomer (a3) used where necessary is preferably from 0.001 mass % to 7 mass %, more preferably from 0.002 mass % to 5 mass %, and even more preferably 0.003 mass % to 4 mass %. In other words, in this case, the upper limit of the content of the surface crosslinking agent based on the total mass of (a1) and/or (a2), (b), and (a3) is preferably 7 mass %, more preferably 5 mass %, and even more preferably 4 mass %. Similarly, the lower limit is preferably 0.001 mass %, more preferably 0.002 mass %, and even more preferably 0.003 mass %. If the content of the surface crosslinking agent falls within the above range, the absorption performance becomes further favorable. The surface crosslinking can be achieved by, for example, a method of spraying an aqueous solution containing the surface crosslinking agent to the water-absorbent resin powder or impregnating the water-absorbent resin powder with the aqueous solution containing the surface crosslinking agent, followed by heating treatment (100 to 200 degrees centigrade) on the water-absorbent resin powder.

The crosslinked polymer (A) may be one polymer or a mixture of two or more polymers.

The surface of the crosslinked polymer (A) may be treated with the surface modifier (B). Examples of the surface modifier (B) include polyvalent metal compounds such as aluminum sulfate, potassium alum, ammonium alum, sodium alum, (poly) aluminum chloride, and hydrates thereof; polycation compounds such as polyethyleneimine, polyvinylamine, and polyallylamine; inorganic fine particles; a surface modifier (B1) containing a hydrocarbon group; a surface modifier (B2) containing a hydrocarbon group having a fluorine atom; and a surface modifier (B3) having a polysiloxane structure.

Examples of the inorganic fine particles include oxides such as silicon oxide (silica), aluminum oxide (alumina), iron oxide, titanium oxide, magnesium oxide, and zirconium oxide, carbides such as silicon carbide and aluminum carbide, nitrides such as titanium nitride, and complexes thereof (e.g., zeolite, talc, etc.). Among them, oxides are preferred, and silicon oxide is further preferred.

The volume average particle size of the inorganic fine particles is preferably from 10 nm to 5000 nm, more preferably from 30 nm to 1000 nm, even more preferably from 50 nm to 750 nm, and most preferably from 90 nm to 500 nm. It is noted that the volume average particle size is measured in a solvent by a dynamic light scattering method. Specifically, the volume average particle size is measured in cyclohexane as a solvent at a temperature of 25 degrees centigrade by using the nano track particle size distribution measuring instrument UPA-EX150 (light source: He—Ne laser) manufactured by Nikkiso Co., Ltd.

The specific surface area of the inorganic fine particles is preferably from 20 $m^2/g$ to 4000 $m^2/g$, more preferably from 30 $m^2/g$ to 3500 $m^2/g$, and even more preferably from 40 $m^2/g$ to 3000 $m^2/g$. If the specific surface area falls within this range, the absorbing performance becomes further favorable. It is noted that the specific surface area is measured according to JIS Z8830:2001 (nitrogen, a volume method, a multipoint method).

The inorganic fine particles are commercially easily available. Examples thereof {hereinafter, trade name (chemical composition, volume average particle size nm, specific surface area $m^2/g$)} include Aerosil 130 (silicon dioxide, 16, 130), Aerosil 200 (silicon dioxide, 12, 200), Aerosil 300 (silicon dioxide, 7, 300), Aerosil 380 (silicon dioxide, 7, 380), Aerosil MOX80 (silicon dioxide, 30, 80), Aerosil COK84 (silicon dioxide, 12, 170), Aerosil OX50T (silicon dioxide, 7, 40), titanium oxide P25 (titanium oxide, 20, 30), and Aluminum Oxide C (aluminum oxide, 13, 100) {Nippon Aerosil Co., Ltd.}; Denka Fused Silica F-300 (silicon dioxide, 11, 160) {Denki Kagaku Kogyo Kabushiki Kaisha}; Microd 850 (silicon dioxide, 13, 150) {Tokai Chemical Industry Co., Ltd.}; Amorphous Silica SP-1 (silicon dioxide, 14, 45) {Nozawa Corporation}; Syloid 622 (silicon dioxide, 17, 350) and Syloid ED50 (silicon dioxide, 8, 400) {Grace Japan Co., Ltd.}; Admafine SO-C1 (complex oxide, 0.1, 20) {Admatechs Company Limited}; Tokusil (silicon dioxide, 2.5, 120) and Reolosil (silicon dioxide, 2.5, 110) {Tokuyama Corporation}; Nipsil E220A (silicon dioxide, 2.5, 130) {Nihon Silica Kogyo K.K.}; and Klebosol 30CAL25 (silicon oxide, 12, 200) {Clariant (Japan) K.K.}.

It should be noted that the crosslinked polymer (A) is hydrophilic, and a hydrophilic inorganic fine particle is used as the inorganic fine particle to generate interaction with the crosslinked polymer (A). Thus, the inorganic fine particle is not hydrophobized, and cannot be regarded as the hydrophobized adsorbent usable for the present invention.

Examples of the surface modifier (B1) containing a hydrocarbon group include polyolefin resins, polyolefin resin derivatives, polystyrene resins, polystyrene resin derivatives, waxes, long-chain fatty acid esters, long-chain fatty acids and salts thereof, long-chain aliphatic alcohols, and mixtures of two or more of them.

Examples of polyolefin resins include a polymer that is obtained by polymerizing an olefin having 2 to 4 carbon atoms such as ethylene, propylene, isobutylene, and isoprene and has a weight average molecular weight from 1,000 to 1,000,000. The content of the olefin component in the polymer is preferably at least 50 mass % in 100% by mass of the polyolefin resin. Specific examples of polyolefin resins include polyethylene, polypropylene, polyisobutylene, poly(ethylene-isobutylene), and isoprene.

As a polyolefin resin derivative, a polymer that has a weight average molecular weight of 1,000 to 1,000,000 and in which a carboxy group (—COOH), 1,3-oxo-2-oxapropylene (—COOCO—), or the like is introduced into a polyolefin resin is preferred. Specific examples thereof include polyethylene thermal degradation products, polypropylene thermal degradation products, maleic acid-modified polyethylene, chlorinated polyethylene, maleic acid-modified polypropylene, ethylene-acrylic acid copolymers, ethylene-maleic anhydride copolymers, isobutylene-maleic anhydride copolymers, maleinated polybutadiene, ethylene-vinyl acetate copolymers, and maleinated products of ethylene-vinyl acetate copolymers.

As a polystyrene resin, a polymer having a weight average molecular weight of 1,000 to 1,000,000 and the like can be used.

As a polystyrene resin derivative, a polymer that contains styrene as an essential constituent monomer and has a weight average molecular weight of 1,000 to 1,000,000 is preferred. The content of styrene is preferably at least 50 mass % in 100 mass % of the polystyrene derivative. Specific examples of polystyrene resin derivatives include styrene-maleic anhydride copolymers, styrene-butadiene copolymers, and styrene-isobutylene copolymers.

Examples of waxes include waxes having a melting point of 50 degrees centigrade to 200 degrees centigrade such as paraffin wax, bees wax, carnauba wax, and beef tallow.

As a long-chain fatty acid ester, an ester of a fatty acid having 8 to 30 carbon atoms and an alcohol having 1 to 12 carbon atoms is preferred. Specific examples of long-chain fatty acid esters include methyl laurate, ethyl laurate, methyl stearate, ethyl stearate, methyl oleate, ethyl oleate, glycerin laurate monoester, glycerin stearate monoester, glycerin oleate monoester, pentaerythritol laurate monoester, pentaerythritol stearate monoester, pentaerythritol oleate monoester, sorbitol laurate monoester, sorbitol stearate monoester, sorbitol oleate monoester, sucrose palmitate monoester, sucrose palmitate diester, sucrose palmitate triester, sucrose stearate monoester, sucrose stearate diester, sucrose stearate triester, and beef tallow. Among them, in light of leakage resistance of the absorbent article, sucrose stearate monoester, sucrose stearate diester, and sucrose stearate triester are preferred, and sucrose stearate monoester and sucrose stearate diester are further preferred.

As a long-chain fatty acid and a salt thereof, a fatty acid having 8 to 30 carbon atoms and a salt thereof are preferred. Examples of fatty acids having 8 to 30 carbon atoms include lauric acid, palmitic acid, stearic acid, oleic acid, dimer acid, and behenic acid. As a metal component of a salt of the fatty acid having 8 to 30 carbon atoms, for example, zinc, calcium, magnesium, or aluminum (hereinafter, they are abbreviated as Zn, Ca, Mg, and Al) is preferred. Specific examples of salts of fatty acids having 8 to 30 carbon atoms include Ca palmitate, Al palmitate, Ca stearate, Mg stearate, and Al stearate. In light of leakage resistance of the absorbent article, as the long-chain fatty acid and a salt thereof, Zn stearate, Ca stearate, Mg stearate, and Al stearate are preferred, and Mg stearate is more preferred.

Examples of long-chain aliphatic alcohols include aliphatic alcohols having 8 to 30 carbon atoms such as lauryl alcohol, palmityl alcohol, stearyl alcohol, and oleyl alcohol. In light of leakage resistance of the absorbent article, as the long-chain aliphatic alcohol, palmityl alcohol, stearyl alcohol, and oleyl alcohol are preferred, and stearyl alcohol is further preferred.

Examples of the surface modifier (B2) containing a hydrocarbon group having a fluorine atom include perfluoroalkanes, perfluoroalkenes, perfluoroaryls, perfluoroalkyl ethers, perfluoroalkylcarboxylic acids or salts thereof, perfluoroalkyl alcohols, and mixtures of two or more of them.

As a perfluoroalkane, an alkane having 4 to 42 fluorine atoms and 1 to 20 carbon atoms is preferred. Examples of perfluoroalkanes include trifluoromethane, pentafluoroethane, pentafluoropropane, heptafluoropropane, heptafluorobutane, nonafluorohexane, tridecafluorooctane, and heptadecafluorododecane.

As a perfluoroalkene, an alkene having 4 to 42 fluorine atoms and 2 to 20 carbon atoms is preferred. Examples of perfluoroalkenes include trifluoroethylene, pentafluoropropene, trifluoropropene, heptafluorobutene, nonafluorohexene, tridecafluorooctene, and heptadecafluorododecene.

As a perfluoroaryl, an aryl having 4 to 42 fluorine atoms and 6 to 20 carbon atoms is preferred. Examples of perfluoroaryls include trifluorobenzene, pentafluorotoluene, trifluoronaphthalene, heptafluorobenzene, nonafluoroxylene, tridecafluorooctylbenzene, and heptadecafluorododecylbenzene.

As a perfluoroalkyl ether, an ether having 2 to 82 fluorine atoms and 2 to 40 carbon atoms is preferred. Examples of perfluoroalkyl ethers include ditrifluoromethyl ether, dipentafluoroethyl ether, dipentafluoropropyl ether, diheptafluoropropyl ether, diheptafluorobutyl ether, dinonafluorohexyl ether, ditridecafluorooctyl ether, and diheptadecafluorododecyl ether.

As a perfluoroalkylcarboxylic acid or a salt thereof, a carboxylic acid having 3 to 41 fluorine atoms and 1 to 21 carbon atoms or a salt thereof is preferred. Examples of perfluoroalkylcarboxylic acids or salts thereof include pentafluoroethanoic acid, pentafluoropropanoic acid, heptafluoropropanoic acid, heptafluorobutanoic acid, nonafluorohexanoic acid, tridecafluorooctanoic acid, heptadecafluorododecanoic acid, or metal salts thereof. As a metal salt, an alkali metal salt or an alkaline earth metal salt is preferred.

As a perfluoroalkyl alcohol, an alcohol having 3 to 41 fluorine atoms and 1 to 20 carbon atoms is preferred. Examples of perfluoroalkyl alcohols include pentafluoroethanol, pentafluoropropanol, heptafluoropropanol, heptafluorobutanol, nonafluorohexanol, tridecafluorooctanol, heptadecafluorododecanol, and ethylene oxide (1 to 20 mol per 1 mol of alcohol) adducts of these alcohols.

Examples of mixtures of two or more of them include a mixture of a perfluoroalkylcarboxylic acid and a perfluoroalkyl alcohol, and, for example, a mixture of pentafluoroethanoic acid and pentafluoroethanol is preferred.

Examples of the surface modifier (B3) having a polysiloxane structure include polydimethylsiloxane; polyether-modified polysiloxanes such as polyoxyethylene-modified polysiloxane and poly(oxyethylene/oxypropylene)-modified polysiloxane; carboxy-modified polysiloxanes; epoxy-modified polysiloxanes; amino-modified polysiloxanes; alkoxy-modified polysiloxanes; and mixtures thereof.

The position of an organic group (modifying group) of a modified silicone such as polyether-modified polysiloxanes, carboxy-modified polysiloxanes, epoxy-modified polysiloxanes, and amino-modified polysiloxanes is not particularly limited, but the position of the organic group may be a side chain of the polysiloxane, both terminals of the polysiloxane, one terminal of the polysiloxane, or combination of a side chain and both terminals of the polysiloxane. Among them, in light of absorption properties, the position is preferably either a side chain of the polysiloxane or combination of a side chain and both terminals of the polysiloxane, and more preferably combination of a side chain and both terminals of the polysiloxane.

Examples of an organic group (modified group) of a polyether-modified polysiloxane include groups containing a polyoxyethylene chain or a poly(oxyethylene-oxypropylene) chain. The number of the oxyethylene units and/or oxypropylene units contained in the polyether-modified polysiloxane is preferably from 2 to 40, more preferably from 5 to 30, even more preferably from 7 to 20, and most preferably from 10 to 15 per one polyether-modified polysiloxane molecule. When the number falls within this range, the absorption properties become further favorable. Also, in the case where an oxyethylene group and an oxypropylene group are contained, the content (mass %) of the oxyethylene group and the oxypropylene group in 100 mass % of the polyether-modified polysiloxane is preferably from 1 mass % to 30 mass %, more preferably from 3 mass % to 25 mass %, and even more preferably from 5 mass % to 20 mass %. When the content of the oxyethylene group and the oxypropylene group falls within the above range, the absorption properties become further favorable.

The polyether-modified polysiloxanes are commercially easily available and, for example, the following commercial products {modification position, type of oxyalkylene} can be preferably exemplified.

Products manufactured by Shin-Etsu Chemical Co., Ltd:
KF-945 {side chain, oxyethylene and oxypropylene},
KF-6020 {side chain, oxyethylene and oxypropylene},
X-22-6191 {side chain, oxyethylene and oxypropylene},
X-22-4952 {side chain, oxyethylene and oxypropylene},
X-22-4272 {side chain, oxyethylene and oxypropylene},
and X-22-6266 {side chain, oxyethylene and oxypropylene}.

Products manufactured by Dow Corning Toray Co., Ltd:
FZ-2110 {both terminals, oxyethylene and oxypropylene},
FZ-2122 {both terminals, oxyethylene and oxypropylene},
FZ-7006 {both terminals, oxyethylene and oxypropylene},
FZ-2166 {both terminals, oxyethylene and oxypropylene},
FZ-2164 {both terminals, oxyethylene and oxypropylene},
FZ-2154 {both terminals, oxyethylene and oxypropylene},
FZ-2203 {both terminals, oxyethylene and oxypropylene},
and FZ-2207 {both terminals, oxyethylene and oxypropylene}.

Examples of an organic group (modifying group) of a carboxy-modified polysiloxanes include groups containing a carboxy group, examples of an organic group (modifying group) of an epoxy-modified polysiloxane include groups containing an epoxy group, and examples of an organic group (modifying group) of an amino-modified polysiloxane include groups containing an amino group (primary, secondary, or tertiary amino group). The content (g/mol) of the organic group (modifying group) in each of these modified silicones is preferably from 200 to 11,000, more preferably from 600 to 8,000, and even more preferably from 1,000 to 4,000, as a carboxy equivalent, an epoxy equivalent, or an amino equivalent. If the content falls within this range, the absorption properties become further favorable. It is noted that the carboxy equivalent is measured according to "16. Total Acid Value Test" of JIS C2101:1999. Also, the epoxy equivalent is obtained according to JIS K7236:2001. Moreover, the amino equivalent is measured according to "8. Potentiometric Titration (base value-hydrochloric acid method)" of JIS K2501:2003.

The carboxy-modified polysiloxanes are commercially easily available and, for example, the following commercial products {modification position, carboxy equivalent (g/mol)} can be preferably exemplified.

Products manufactured by Shin-Etsu Chemical Co., Ltd.: X-22-3701E {side chain, 4000}, X-22-162C {both terminals, 2300}, and X-22-3710 {one terminal, 1450}.

Products manufactured by Dow Corning Toray Co., Ltd.: By 16-880 {side chain, 3500}, BY 16-750 {both terminals, 750}, BY 16-840 {side chain, 3500}, and SF8418 {side chain, 3500}.

The epoxy-modified polysiloxanes are commercially easily available and, for example, the following commercial products {modification position, epoxy equivalent} can be preferably exemplified.

Products manufactured by Shin-Etsu Chemical Co., Ltd.: X-22-343 {side chain, 525}, KF-101 {side chain, 350}, KF-1001{side chain, 3500}, X-22-2000 {side chain, 620}, X-22-2046 {side chain, 600}, KF-102 {side chain, 3600}, X-22-4741 {side chain, 2500}, KF-1002 {side chain, 4300}, X-22-3000T {side chain, 250}, X-22-163 {both terminals, 200}, KF-105 {both terminals, 490}, X-22-163A {both terminals, 1000}, X-22-163B {both terminals, 1750}, X-22-163C {both terminals, 2700}, X-22-169AS {both terminals, 500}, X-22-169B {both terminals, 1700}, X-22-173DX {one terminal, 4500}, and X-22-9002 {side chain and both terminals, 5000}.

Products manufactured by Dow Corning Toray Co., Ltd.: FZ-3720 {side chain, 1200}, BY 16-839 {side chain, 3700}, SF 8411 {side chain, 3200}, SF 8413 {side chain, 3800}, SF 8421 {side chain, 11000}, BY 16-876 {side chain, 2800}, FZ-3736 {side chain, 5000}, BY 16-855D {side chain, 180}, and BY 16-8 {side chain, 3700}.

The amino-modified silicones are commercially easily available and, for example, the following commercial products {modification position, amino equivalent} can be preferably exemplified.

Products manufactured by Shin-Etsu Chemical Co., Ltd.: KF-865 {side chain, 5000}, KF-864 {side chain, 3800}, KF-859 {side chain, 6000}, KF-393 {side chain, 350}, KF-860 {side chain, 7600}, KF-880 {side chain, 1800}, KF-8004 {side chain, 1500}, KF-8002 {side chain, 1700}, KF-8005 {side chain, 11000}, KF-867 {side chain, 1700}, X-22-3820W {side chain, 55000}, KF-869 {side chain, 8800}, KF-861 {side chain, 2000}, X-22-3939A {side chain, 1500}, KF-877 {side chain, 5200}, PAM-E {both terminals, 130}, KF-8010 {both terminals, 430}, X-22-161A {both terminals, 800}, X-22-161B {both terminals, 1500}, KF-8012 {both terminals, 2200}, KF-8008 {both terminals, 5700}, X-22-1660B-3 {both terminals, 2200}, KF-857 {side chain, 2200}, KF-8001 {side chain, 1900}, KF-862 {side chain, 1900}, and X-22-9192 {side chain, 6500}.

Products manufactured by Dow Corning Toray Co., Ltd.: FZ-3707 {side chain, 1500}, FZ-3504 {side chain, 1000}, BY 16-205 {side chain, 4000}, FZ-3760 {side chain, 1500}, FZ-3705 {side chain, 4000}, BY 16-209 {side chain, 1800}, FZ-3710 {side chain, 1800}, SF 8417 {side chain, 1800}, BY 16-849 {side chain, 600}, BY 16-850 {side chain, 3300}, BY 16-879B {side chain, 8000}, BY 16-892 {side chain, 2000}, FZ-3501 {side chain, 3000}, FZ-3785 {side chain, 6000}, BY 16-872 {side chain, 1800}, BY 16-213 {side chain, 2700}, BY 16-203 {side chain, 1900}, BY 16-898 {side chain, 2900}, BY 16-890 {side chain, 1900}, BY 16-893 {side chain, 4000}, FZ-3789 {side chain, 1900}, BY 16-871 {both terminals, 130}, BY 16-853C {both terminals, 360}, and BY 16-853U {both terminals, 450}.

Examples of mixtures of them include a mixture of polydimethylsiloxane and a carboxyl-modified polysiloxane, and a mixture of a polyether-modified polysiloxane and an amino-modified polysiloxane.

As the surface modifier (B), in light of absorption properties, the surface modifier (B3) having a polysiloxane structure and inorganic fine particles are preferred, and amino-modified polysiloxanes, carboxy-modified polysiloxanes, and silica are more preferred.

The method for treating the crosslinked polymer (A) with the surface modifier (B) is not particularly limited, as long as treatment is conducted such that the surface modifier (B) is present on the surface of the crosslinked polymer (A). However, from the standpoint that the amount of the surface modifier (B) on the surface is controlled, it is preferred that the surface modifier (B) is mixed with a dried product of the crosslinked polymer (A), not with a water-containing gel of the crosslinked polymer (A) or a polymerization liquid that is prior to polymerization of the crosslinked polymer (A). It is noted that it is preferred that the mixing is uniformly conducted.

The shape of the water-absorbent resin powder is not particularly limited, and examples thereof include an indefinite crushed shape, a scale shape, a pearl shape, and a rice grain shape. Among them, the indefinite crushed shape is preferred from the standpoint that the powder in such a shape can be well entangled with fibrous materials in applications such as a disposable diaper and there is little possibility of the powder falling off from the fibrous materials.

The water-absorbent resin powder can contain additives such as an antiseptic, a fungicide, an antibacterial, an antioxidant, a ultraviolet absorber, a coloring agent, a perfuming agent, a deodorizer, an inorganic powder, and an organic fibrous material. Examples of such additives include those exemplified in Japanese Patent Publication No. 2003-225565 and Japanese Patent Publication No. 2006-131767. When these additives are contained, the content (mass %) of the additives with respect to the crosslinked polymer (A) (100 mass %) is preferably from 0.001 mass % to 10 mass %, more preferably from 0.01 mass % to 5 mass %, even more preferably from 0.05 mass % to 1 mass %, and most preferably from 0.1 mass % to 0.5 mass %.

Hydrophobized Adsorbent

The hydrophobized adsorbent that can be used in the present invention is not particularly limited, as long as it can physically adsorb water vapor and is hydrophobized. Here, "physically adsorb" refers to adsorption not accompanied by any chemical reactions. Examples of the hydrophobization include: a method of causing hydrophilic functional groups (e.g., carboxy group, hydroxy group, silanol group) existing on the surface of the adsorbent to react with a hydrophobization agent; and a method of removing hydrophilic functional groups existing on the surface of the adsorbent through a heat treatment. At least one part of the surface of the hydrophobized adsorbent is preferably hydrophobized.

Examples of the hydrophobized adsorbent include general adsorbents (e.g., silica, alumina, zeolite, activated carbon) having hydrophobization treatment performed thereon. Specific examples thereof include hydrophobized calcium carbonate, hydrophobized bentonite, hydrophobized kaolinite, hydrophobized silica, hydrophobized alumina, hydrophobized zeolite (hydrophobized silica alumina), and hydrophobized activated carbon. Among these, hydrophobized silica, hydrophobized alumina, hydrophobized activated carbon, and hydrophobized zeolite are preferable.

It should be noted that it is generally known that zeolite becomes more hydrophobic when its silica content becomes higher. Although the zeolite that does not include $Al_2O_3$ may be referred to as a hydrophobic silicalite, it should also be noted that the zeolite that does not include $Al_2O_3$ is not qualified as the hydrophobized adsorbent used in the present invention. In addition, although carbon which is the main component of activated carbon is hydrophobic, oxygen atoms are introduced on the surface of the activated carbon in the form of carboxyl groups and hydroxyl groups during the production of activated carbon. Therefore, unlike general carbon, activated carbon shows hydrophilicity. By treating the carboxy groups and hydroxy groups etc., located on the surface of the activated carbon with a hydrophobization agent, the hydrophobized activated carbon is produced.

Examples of the hydrophobization agent include: a hydrophobization agent including a hydrocarbon group (C1); a hydrophobization agent including a hydrocarbon group with a fluorine atom (C2); a hydrophobization agent having a polysiloxane structure (C3); a silane coupling agent (C4); and a silylation reagent (C5). As the hydrophobization agent including a hydrocarbon group (C1), the hydrophobization agent including a hydrocarbon group with a fluorine atom (C2), and the hydrophobization agent having a polysiloxane structure (C3); those illustrated as surface modifiers (B) for the crosslinked polymer (A) can be used.

Examples of the silane coupling agent (C4) include, but not particularly limited to: alkylalkoxysilanes such as methyltrimethoxysilane, dimethyldimethoxysilane, and dimethyldiethoxysilane; vinylsilanes such as vinyltrimethoxysilane and vinyltriethoxysilane; aminosilanes such as gamma-aminopropyl triethoxysilane, N-(beta-aminoethyl)-gamma-aminopropyl trimethoxysilane, and N-(beta-aminoethyl)-gamma-aminopropyl methyldimethoxysilane; epoxysilanes such as gamma-glycidoxypropyl trimethoxysilane and beta-glycidoxypropyl methyldimethoxysilane; methacryloxysilanes such as gamma-methacryloxypropyl trimethoxysilane and gamma-methacryloxypropyl methyldimethoxysilane; and mercaptosilanes such as gamma-mercaptopropyl trimethoxysilane (3-mercaptopropyl trimethoxysilane).

Examples of the silylation reagent (C5) include, but not particularly limited to: hexamethyldisilazane, trimethylsilyl chloride, triethylsilyl chloride, t-butyldimethylsilyl chloride, triisopropylsilyl chloride, chloromethyltrimethylsilane, t-butyldimethylsilane, and hexamethyldisilane.

Examples of producing the hydrophobized silica include: a method of surface-treating silica surface with a hydrophobization agent (e.g., polyethylene wax) including a hydrocarbon group; a method of hydrophobizing silica surface with a hydrophobization agent (high molecular weight organopolysiloxane) having a polysiloxane structure; a method of hydrophobizing silica surface with a silylation reagent (hexamethyldisilazane (HMDS)) and a hydrophobization agent (organopolysiloxane) having a polysiloxane structure; a method of obtaining hydrophobized silica by causing silica to react with methylchlorosilane or a silane coupling agent; a method of causing a reaction with hexamethyldisilazane (HMDS) in the presence of water vapor and a basic gas such as ammonia and amine; and a method of introducing a reactive amino group on the surface of hydrophilic silica by causing it to react with an amino group containing silane coupling agent (aminoalkylsilane compound), and obtaining a reaction product between the amino group and a specific compound (a compound having a hydrocarbon group).

Furthermore, the hydrophobized silica is easily available from the market, and, for example, preferably includes the following products. Specific examples thereof include (the following shows product name (chemical composition, volume average particle diameter (nm), and specific surface area ($m^2/g$)): Aerosil R972 (silicon dioxide, 16, 110); Aerosil R974 (silicon dioxide, 12, 170); Aerosil R104 (silicon dioxide, 12, 150); Aerosil R106 (silicon dioxide, 7, 250); Aerosil R202 (silicon dioxide, 14, 100); Aerosil R805 (silicon dioxide, 12, 150); Aerosil R812 (silicon dioxide, 7, 260); Aerosil R812S (silicon dioxide, 7, 220); Aerosil R816 (silicon dioxide, 12, 190); Aerosil R7200 (silicon dioxide, 12, 150); Aerosil R8200 (silicon dioxide, 12, 160); Aerosil R9200 (silicon dioxide, 12, 170); and Aerosil R711 (silicon dioxide, 12, 150) (Nippon Aerosil Co., Ltd.).

Examples of producing the hydrophobized alumina and hydrophobized zeolite include a method of obtaining those by causing a counterion of an aluminum cation to react with a hydrophobic cation (e.g., a trialkylammonium having a carbon number of 8 to 24). Examples of producing the hydrophobized activated carbon include a method similar to that for producing the hydrophobized silica.

The specific surface area of the hydrophobized adsorbent used in the present invention is, for a standpoint of water vapor adsorption performance, preferably 200 $m^2/g$ or more, and more preferably 220 $m^2/g$ or more. Although a specific surface area is preferably as large as possible from a standpoint of adsorbing water vapor, the specific surface area is more preferably 10,000 $m^2/g$ or less. This is because, if the specific surface area is larger than 10,000 $m^2/g$, the adsorbent may break when an impact is applied thereto and water-vapor adsorptive property tends to deteriorate. It should be noted the specific surface area is specific surface area measured by the BET multipoint method using krypton gas as adsorption gas.

The volume average particle size of the hydrophobized adsorbent is not particularly limited. From a standpoint of workability and operability, the volume average particle size is preferably 2 nm or more, more preferably 4 nm or more, and further preferably 5 nm or more, and is preferably than 5 mm or less, more preferably 4 mm or less, and further preferably 3 mm or less. If an ultra-fine powder (several nm to several micrometers) is directly used, since the ultra-fine powder may escape from the absorbent article, the ultra-fine powder is preferably fixed on the absorbent body using a binder such as a hot-melt adhesive. In addition, the ultra-fine powder (several nm to several micrometers) may be granulated to have a larger particle size for use. It should be noted that the volume average particle size is measured in cyclohexane as a solvent at a temperature of 25 degrees centigrade by using a Nanotrac particle size distribution measuring device UPA-EX150 (light source: He—Ne laser) manufactured by Nikkiso Co., Ltd. Furthermore, those having a large particle size (0.02 micrometers to 2,800 micrometers) are measured in a solvent with laser diffraction using a light scattering method. Specifically, the particle size is measured at a temperature of 25 degrees centigrade by using a Microtrac particle size distribution measuring device MT300011 manufactured by Nikkiso Co., Ltd.

Although the hydrophobized adsorbent is hydrophobic, its hydrophobicity is preferably 1 minute or more, more preferably 2 minutes or more, and further preferably 5 minutes or more. The upper limit of hydrophobicity is not particularly limited, and is ordinarily about 6000 minutes. The hydrophobicity of the hydrophobized adsorbent can be determined by the time (minute) required for half or more of the hydrophobized adsorbent (1.0 g) to precipitate in the distilled water (100 ml) at 25 degrees centigrade.

The absorbent body used in the present invention includes, with respect to 100 parts by mass of the water absorbent resin powder having an absorption speed in a range from 6 seconds to 60 seconds determined by a vortex method, the hydrophobized adsorbent in an amount of 0.01 part by mass or more, more preferably 0.1 part by mass or more, and further preferably 1 part by mass or more, and preferably includes the hydrophobized adsorbent in an amount of 20 parts by mass or less, more preferably 18 parts by mass or less, and further preferably 15 parts by mass or less. The above described range is preferable because of the following reasons. If the amount of the hydrophobized adsorbent is 0.01 part by mass or more with respect to 100 parts by mass of the water absorbent resin powder, the water-vapor adsorptive property is enhanced for preventing the condensation on the absorbent article, while if the amount is 20 parts by mass or less, further excellent texture is obtained on the absorbent article.

Absorbent Article

Next, the structure of the absorbent article of the present invention will be described. The absorbent article of the present invention comprises an absorbent body composed of at least one absorption layer, wherein the absorbent body includes a hydrophobized adsorbent and a water absorbent resin powder having (a) an absorption speed in a range from 6 seconds to 60 seconds determined by a vortex method.

The absorbent body of the absorbent article of the present invention is composed of at least one absorption layer. The absorption layer preferably includes, as a water absorbent material, the water absorbent resin powder having (a) an absorption speed in a range from 6 seconds to 60 seconds determined by a vortex method. The absorption layer may further include, as the water absorbent material, a fiber base material or a water absorbent resin powder having an absorption speed of less than 6 seconds or more than 60 seconds determined by the vortex method. The thin absorption layer can be formed, if only the water absorbent resin powder is contained as the water absorbent material. The absorption layer having a fiber base material is excellent in body fluid dispersibility. Examples of the fiber base material include fiberized pulp, thermal bonding fibers, and the like. As the fiberized pulp, pulp fibers known in the art can be used. Thermal bonding fibers are used to enhance shape-retention. Specific examples of the thermal bonding fibers include polyolefin fibers such as polyethylene and polypropylene, polyester fibers, and composite fibers. The absorption layer can be obtained by, for example, mixing a granular water absorbent resin powder and a hydrophilic fiber assembly layer such as pulverized pulp fibers and cellulose fibers, fixing them onto a liquid permeable nonwoven fabric sheet or a paper sheet such as a tissue paper, or wrapping them using a liquid permeable nonwoven fabric sheet, and molding them in a predetermined shape such as a rectangular shape, a hourglass shape, a gourd shape, a battledore shape, and the like.

The absorbent body includes a hydrophobized adsorbent. The hydrophobized adsorbent may be disposed inside an absorption layer or may be disposed outside the absorption layer. When the hydrophobized adsorbent is disposed inside the absorption layer, the hydrophobized adsorbent may be mixed with the water absorbent material, or the hydrophobized adsorbent may be attached to the surface of a layer formed by the water absorbent material. Furthermore, when the hydrophobized adsorbent is disposed outside the absorption layer, the hydrophobized adsorbent may be directly attached to the surface of the absorption layer, or an adsorption sheet formed by having the hydrophobized adsorbent supported (attached) on a liquid permeable nonwoven fabric sheet or the like may be laminated on the absorption layer. It should be noted that when attaching the hydrophobized adsorbent to the surface of the water absorbent material layer, the absorption layer, or the liquid permeable nonwoven fabric sheet, the hydrophobized adsorbent may be uniformly sprayed on a whole surface thereof, or may be sprayed in multiple streaks extending continuously (or intermittently) in one direction. In the absorbent article of the present invention, the absorbent body preferably includes the hydrophobized adsorbent at a location closer to the skin surface side than the water absorbent material. This is because having the hydrophobized adsorbent on the skin surface side further enhances the water vapor absorption effect. From this standpoint, when there are two or more layers of the absorption layers forming the absorbent body of the absorbent article of the present invention, the hydrophobized adsorbent is preferably included in the very top layer (the layer located closest to the skin surface side).

The absorbent article of the present invention preferably includes, for example, a surface sheet material disposed on a skin surface side of the absorbent body and a liquid impermeable exterior sheet material disposed on an external surface side of the absorbent body, wherein at least one part of the surface sheet material is liquid permeable.

In one preferable embodiment of the present invention, the disposable diaper of the present invention preferably comprises a liquid permeable top sheet, a liquid impermeable back sheet, and an absorbent body interposed between the liquid permeable top sheet and liquid impermeable back sheet, wherein the absorbent body contains the hydrophobized adsorbent and the water absorbent resin powder having an absorption speed in a range from 6 seconds to 60 seconds determined by the vortex method. In this case, the liquid permeable top sheet corresponds to the surface sheet material, and the liquid impermeable back sheet corresponds to the exterior sheet material. The liquid impermeable back sheet preferably has moisture permeability. In addition, if necessary, side sheets may be provided on both sides in the width direction of the liquid permeable top sheet. The side sheets are joined to the upper parts of both side-edge portions in the width direction of the top sheet, and portions of the side sheet inwards of joining points form one pair of rise flaps along both side edges of the absorbent body.

In another embodiment of the present invention, the disposable article preferably comprises a laminated body composed of an inner sheet and an outer sheet, and an absorbent body disposed on a skin surface side of the laminated body and between a liquid permeable top sheet and a liquid impermeable back sheet, wherein the absorbent body includes the hydrophobized adsorbent and the water absorbent resin powder having an absorption speed in a range from 6 seconds to 60 seconds determined by the vortex method. In this case, the liquid permeable top sheet corresponds to the surface sheet material, and the laminated body composed of the inner sheet and the outer sheet corresponds to the exterior sheet material. On upper parts of both side-edge portions in the width direction of the liquid permeable top sheet, one pair of rise flaps may be formed along both side edges of the absorbent body.

With respect to the terms of each part of the disposable diaper, when the diaper is worn, a portion placed on the abdominal side of a wearer is referred to as a front abdominal portion, a portion placed on the hip side of the wearer is referred to as a back portion, and a portion located between the front abdominal portion and the back portion and placed on the crotch of the wearer is referred to as a crotch portion. When the joining between the front abdominal portion and the back portion is released and the main body of the diaper is planarly unfolded, the crotch portion is a portion located in the middle when the diaper is divided in three in its front-back direction, and refers to a portion whose both side edges in the width direction are not joined when the diaper is assembled into a pants shape. A front-back direction of the diaper is a direction from the front abdominal portion to the back portion of the diaper, and the width direction of the diaper is a direction that is on the same surface as the diaper when the diaper is planarly unfolded and that is orthogonal to the front-back direction.

The disposable diaper (absorbent article) may be: a pants-type diaper that has a front abdominal portion, a back portion, and a crotch portion located between them, and that has a waist opening and one pair of leg openings formed when the front abdominal portion and the back portion are joined to respective side edges; or an open-type diaper that is used by joining a front abdominal portion and a back portion together with a securing tape or the like.

From a standpoint of preventing leakage, the sheet material forming the exterior sheet material is preferably a liquid impermeable or a water-repellent nonwoven fabric. For example, the exterior sheet material includes water-repellent or liquid impermeable nonwoven fabrics (e.g., spunbond nonwoven fabrics, melt-blown nonwoven fabrics, and SMS (span bond-melt blow-span bond) nonwoven fabrics) formed from a hydrophobic fiber (e.g., polypropylene, polyethylene, polyester, polyamide, and nylon), and water-repellent or liquid impermeable plastic films. These liquid impermeable or water-repellent nonwoven fabrics have moisture permeability. When a plastic film is used as the exterior sheet material, from a standpoint of improving comfort of the wearer by preventing dampness, a plastic film having moisture permeability (breathability) is preferably used.

The disposable diaper (absorbent article) is preferably provided with a waist elastic member along a waist opening edge of the front abdominal portion or the back portion. The waist elastic members serve to prevent leakage of excrement such as urine or the like from the back side or the abdominal portion side even when the wearer is lying down. Multiple waist elastic members may be provided.

The disposable diaper (absorbent article) is preferably provided with a leg elastic member along a leg opening edge. The leg elastic member serves to prevent leakage of excrement such as urine or the like from the leg opening edge. It should be noted that the leg opening edge is the edge of the circumference of the leg opening of the disposable diaper. Multiple leg elastic members may be provided.

The disposable diaper (absorbent article) is preferably provided with multiple torso circumference elastic members at the front abdominal portion and/or the back portion in the width direction of the diaper main body. The torso circumference elastic members serve to improve fitting of the diaper at the circumference of the hip and lower abdominal region.

As each of the elastic members, an elastic expandable material ordinarily used for disposable diapers can be used, such as polyurethane threads, polyurethane films, natural rubbers, etc. Each of the elastic members is preferably, in a stretched state, fixed to exterior sheet materials and/or surface sheet materials using a hot-melt adhesive. As the hot-melt adhesive, a rubber based hot melt adhesive is preferable.

The surface sheet material whose at least one part is liquid permeable is disposed on the skin surface side of the disposable diaper (absorbent article). The surface sheet material of the diaper has a top sheet made of, for example, a nonwoven fabric material. The top sheet made of a nonwoven fabric material has liquid permeability.

The liquid permeable top sheet constituting the surface sheet material of the disposable diaper is suitable for quickly capturing and transferring fluid in excrement of the wearer to the absorbent body interposed between the surface sheet material and the exterior sheet material.

The liquid permeable top sheet is a liquid permeable sheet material, for example, a nonwoven fabric formed from a hydrophilic fiber; and quickly captures and transfers fluid in excrement of the wearer to the absorbent body. Examples of the nonwoven fabric used as the top sheet include point-bond nonwoven fabrics, air-through nonwoven fabrics, spun lace nonwoven fabrics, and spunbond nonwoven fabrics. As the hydrophilic fiber forming these nonwoven fabrics, cellulose, rayon, cotton, and the like are ordinarily used. It should be noted that, as the top sheet, a liquid permeable nonwoven fabric formed from a hydrophobic fiber (e.g., polypropylene, polyethylene, polyester, polyamide, and nylon) whose surface is hydrophilized with a surfactant may be used.

The liquid impermeable side sheets may be provided on both sides in the width direction of the liquid permeable top sheet. The liquid impermeable side sheets preferably form rise flaps. The rise flaps prevent side-way leakage of urine etc., and quickly transfer fluid in excrement to the absorbent body.

Rise elastic members are preferably provided at end portions (end portion on the wearer side) of the rise flaps. As a result of contractive force by the rise elastic members, the rise flaps that rise on the wearer side are formed to prevent side-way leakage of urine etc.

In the following, although the absorbent article of the present invention will be described with reference to the drawings, the present invention is not limited to the embodiments shown by the drawings.

FIGS. 1 to 4 are schematic sectional views showing preferable embodiments of the absorbent body composed of at least one absorption layer and included in the absorbent article of the present invention. In FIGS. 1 to 4, with respect to C direction on the paper surface, the upper side is the skin surface side and the lower side is the external surface side.

An absorbent body 2 shown in FIG. 1 is composed of an absorption layer including a water absorbent resin powder 6 having an absorption speed in a range from 6 seconds to 60 seconds determined by the vortex method, a hydrophobized adsorbent 4, and a fiber base material 8. The absorbent body 2 shown in FIG. 2 is composed of a mixture layer including the water absorbent resin powder 6 and the fiber base material 8, and an adsorption layer that is disposed on top of the mixture layer and includes the hydrophobized adsorbent 4. The absorbent body 2 shown in FIG. 3 is composed of an absorption layer 2*b* including the water absorbent resin powder 6 and the fiber base material 8, and an adsorption sheet 4*a* (in which the hydrophobized adsorbent 4 is supported by a liquid permeable nonwoven fabric sheet 10) that is disposed on top of the absorption layer 2*b*. In the embodiment shown in FIG. 2 or FIG. 3, the hydrophobized adsorbent 4 disposed on top of the mixture layer or the liquid permeable nonwoven fabric sheet may be arranged on the whole area of the top surface of the mixture layer or the liquid permeable nonwoven fabric sheet, or may be arranged on one part of the top surface of the mixture layer. The absorbent body 2 shown in FIG. 4 includes an absorption layer 2*a*, and the absorption layer 2*b* disposed below the absorption layer 2*a*. In the absorbent body 2 shown in FIG. 4, the absorption layer 2*a* includes the water absorbent resin powder 6 and the hydrophobized adsorbent 4, and the absorption layer 2*b* includes the water absorbent resin powder 6 and the fiber base material 8. It should be noted that, in FIGS. 1 to 4, although embodiments in which each of the absorption layers is covered with a liquid permeable sheet such as tissue paper are illustrated, it is not necessary to have the absorption layers covered with a liquid permeable sheet. As shown in FIGS. 1 to 4, by having the hydrophobized adsorbent 4 on the skin surface side, the absorbent body has a further higher water vapor adsorption effect. In FIGS. 1 to 4, although an absorbent body having a single-layer or two-layer structure is shown, the absorbent body may have a structure with three or more layers.

FIG. 5 shows one example of a pants-type disposable diaper (absorbent article) (expansion plan). A pants-type disposable diaper 1 includes the front abdominal portion 3 and the back portion 5 in the length direction A, and the crotch portion 7 between the front abdominal portion 3 and the back portion 5. The front abdominal portion 3 makes contact with the abdominal side of the wearer, and the back portion 5 makes contact with the hip side of the wearer. The crotch portion 7 has provided thereon the notches 9 so as to follow the circumference of the legs of the wearer. In the pants-type disposable diaper 1 in FIG. 5, side edges 3a of the front abdominal portion 3 are joined to side edges 5a of the back portion 5 to form the pants-type disposable diaper 1 having a waist opening and one pair of leg openings.

In the pants-type disposable diaper 1, an absorbent main body 13 is attached on the skin surface side of the exterior sheet material 11. The absorbent main body 13 extends in the length direction A from the center of the crotch portion 7.

On the pants-type disposable diaper 1, the front-side waist elastic member 15 and the back-side waist elastic member 17 are attached in a stretched state in the width direction B along the end edges 12 of the exterior sheet material 11. In addition, front-side leg elastic members 19 and back-side leg elastic members 21 are attached along the notches 9 in a stretched state. On the front abdominal portion 3 and the back portion 5, a front-side torso circumference elastic member 23 and a back-side torso circumference elastic member 25 are respectively attached in the width direction B in a stretched state between the waist elastic member and the leg elastic member. Through contraction of each of the elastic members, the pants-type disposable diaper 1 fits onto the wearer.

FIG. 6 is a schematic cross sectional view along line I-I of the pants-type disposable diaper in FIG. 5. The structure of the pants-type disposable diaper 1 will be described with reference to FIG. 6. The exterior sheet material 11 includes the outer sheet 11a and the inner sheet 11b, and, between both of the sheets, the waist elastic members 15 and 17, the leg elastic members 19 and 21, the torso circumference elastic members 23 and 25 attached in a stretched state. The outer sheet 11a is longer than the inner sheet 11b in the length direction, and has formed thereon folded portions 14 that are folded toward inner surface sides (skin surface side) at the end edges 12.

The absorbent main body 13 is attached on the skin surface side of the exterior sheet material 11. The absorbent main body 13 includes the absorbent body 2 (2a, 2b), the top sheet 27 made of a nonwoven fabric material and disposed on the skin surface side of the absorbent body 2, and a liquid impermeable back sheet 29 provided on the external surface side of the absorbent body 2. On the pants-type disposable diaper 1, a front-side end holding sheet 31 and a back-side end holding sheet 33 are provided so as to cover end portions in the length direction of the absorbent main body 13 at the front abdominal portion 3 and the back portion 5 on the inner surface of the inner sheet 11b.

FIG. 7 is a schematic cross sectional view along line II-II of the pants-type disposable diaper in FIG. 5. As shown in FIG. 7, the side sheets 35 made of a nonwoven fabric material are joined on both side-edge portions in the width direction of the top sheet 27 made of a nonwoven fabric material. The side sheets 35 form rise flaps that rise toward the skin of the wearer through contractive force of the elastic members 37 attached in the length direction in a stretched state, and act as a barrier for preventing side-way leakage of urine etc.

FIG. 8 is a schematic sectional view for describing another preferable embodiment of the disposable diaper 1. The pants-type disposable diaper 1 includes a liquid permeable top sheet 27, a liquid impermeable back sheet 29, and the absorbent body 2 interposed between the liquid permeable top sheet 27 and the liquid impermeable back sheet 29. Liquid impermeable side sheets 35 are joined to the top of both side-edge portions of the liquid permeable top sheet 27. Portions of the side sheets 35 inward of the joining points 34 form rise flaps that rise toward the skin of the wearer. Portions of the side sheet outward of the joining points 34 extend outward from side edges of the absorbent body 2, and are joined onto the back sheet 29. The surface sheet material includes the liquid permeable top sheet 27 and the liquid impermeable side sheets 35. The exterior sheet material includes the liquid impermeable back sheet 29.

Specific examples of the absorbent article of the present invention include absorbent articles which absorb the fluid excreted from human body such as a disposable diaper, a sanitary napkin, an incontinence pad, and a breast milk pad.

EXAMPLES

Hereinafter, the present invention will be described in detail by means of examples. However, the present invention is not limited to the examples below, and changes and embodiments that do not depart from the gist of the present invention are included in the scope of the present invention.
<<Evaluation Methods>>
(Method for Measuring Water-Absorption Speed by a Vortex Method)

50 mL of a saline (0.9 wt % sodium chloride solution) and a magnetic stir tip (a diameter at center portion: 8 mm, a diameter at both end portions: 7 mm, length: 30 mm, the surface is coated with a fluororesin) are placed into a 100-mL glass beaker, and the beaker is placed on a magnetic stirrer (HPS-100 manufactured by AS ONE Corporation). The rotational speed of the magnetic stirrer is adjusted to 600 plus or minus 60 rpm, and the saline is stirred. 2.0 g of a sample is added to the solution at the center of the vortex of the saline being stirred, and the water-absorption speed (seconds) of the water-absorbent resin powder is measured according to JIS K 7224 (1996). Specifically, a stopwatch is started at the time when the addition of the water-absorbent resin powder, which is the sample, to the beaker is completed. The stopwatch is stopped at the time when the stirrer tip is covered with the test solution (the time when the vortex disappears and the surface of the solution becomes flat), and the time (seconds) is recorded as a water-absorption speed. The measurement is conducted five times (n=5), the highest and lowest values are removed, and the average of the remaining three values is regarded as a measured value. It is noted that these measurements are conducted at 23 plus or minus 2 degrees centigrade and a relative humidity of 50 plus or minus 5%, and samples are stored in the same environment for 24 hours or longer prior to the measurements and then are subjected to the measurements.
(Moisture Absorption Blocking Ratio)

10.0 g of a sample is uniformly placed into an aluminum cup having a bottom diameter of 52 mm and a height of 22 mm (a foil container, product number: 107, manufactured by Toyo Aluminium Ecko Products Co., Ltd.), and the cup is kept still in a constant temperature and humidity chamber at 40 degrees centigrade and a relative humidity of 80% RH for 3 hours. Then, the sample is lightly sieved with a 12-mesh (opening 1.4 mm) wire mesh, the mass of powdered matter of the measurement sample that has caused blocking due to moisture absorption and has not passed through the 12 mesh and the mass of the sample that has passed through the 12 mesh are measured, and a moisture absorption blocking ratio which is an object is calculated according to the following equation.

Moisture absorption blocking ratio (%)=(mass of sample not passing through 12 mesh after being kept still)/(mass of sample not passing through 12 mesh after being kept still+mass of sample passing through 12 mesh after being kept still)× 100

The measurement is conducted five times (n=5), the highest and lowest values are removed, and the average of the remaining three values is regarded as a measured value. It is noted that these measurements are conducted at 23 plus or minus 2 degrees centigrade and a relative humidity of 50 plus or minus 5%, and samples are stored in the same environment for 24 hours or longer prior to the measurements and then are subjected to the measurements.

(Method for Measuring Absorption Ratio)

Measurement of an absorption ratio is conducted according to JIS K 7223 (1996). A nylon mesh having openings of 63 micrometers (JIS Z8801-1:2000) is cut into a rectangle having a width of 10 cm and a length of 40 cm and folded in half at a center in its longitudinal direction, and both ends thereof are heat-sealed, to produce a nylon bag having a width of 10 cm (inside dimension: 9 cm) and a length of 20 cm. 1.00 g of a measurement sample is precisely weighted and placed into the produced nylon bag such that the sample is uniform at the bottom of the nylon bag. The nylon bag containing the sample is immersed in a saline. After 60 minutes from start of the immersion, the nylon bag is taken out from the saline, and is hung vertically for 1 hour to drain the nylon bag. Then, the mass (F1) of the sample is measured. In addition, the same operation is conducted without using any sample, and a mass F0 (g) at that time is measured. Then, an absorption ratio which is an object is calculated according to the following equation from these masses F1 and F0 and the mass of the sample.

Absorption ratio (g/g)=($F1$–$F0$)/mass of sample (Method for Measuring Water Retention Amount)

Measurement of a water retention amount is conducted according to JIS K 7223 (1996). A nylon mesh having openings of 63 micrometers (JIS Z8801-1:2000) is cut into a rectangle having a width of 10 cm and a length of 40 cm and folded in half at a center in its longitudinal direction, and both ends thereof are heat-sealed, to produce a nylon bag having a width of 10 cm (inside dimension: 9 cm) and a length of 20 cm. 1.00 g of a measurement sample is precisely weighted and placed into the produced nylon bag such that the sample is uniform at the bottom of the nylon bag. The nylon bag containing the sample is immersed in a saline. After 60 minutes from start of the immersion, the nylon bag is taken out from the saline, and is hung vertically for 1 hour to drain the nylon bag. Then, the nylon bag is dehydrated using a centrifugal hydroextractor (model H-130C special type, manufactured by Kokusan Co., Ltd.). The dehydrating conditions are 143 G (800 rpm) and 2 minutes. A mass (R1) after the dehydration is measured. In addition, the same operation is conducted without using any sample, and a mass R0 (g) at that time is measured. Then, a water retention amount which is an object is calculated according to the following equation from these masses R1 and R0 and the mass of the sample.

Water retention amount (g/g)=($R1$–$R0$–mass of sample)/mass of sample (Method for Measuring Liquid-Passing Speed Under Load)

In a 100-mL glass beaker, 0.32 plus or minus 0.005 g of a water-absorbent resin powder that is a sample is immersed in 100 mL of a saline (0.9 wt % sodium chloride solution) and allowed to stand for 60 minutes, thereby swelling the water-absorbent resin powder. Separately, a filtration cylindrical tube is prepared in which a wire mesh (openings: 150 micrometers, a bio-column sintered stainless steel filter 30SUS sold by Sansyo Co., Ltd) and a narrow tube (inner diameter: 4 mm, length: 8 cm) equipped with a cock (inner diameter: 2 mm) are provided at the lower end of an opening portion of a cylinder (inner diameter: 25.4 mm) that stands vertically. All the content within the beaker including the swollen measurement sample is placed into the cylindrical tube in a state where the cock is closed. Next, a cylindrical bar that has a diameter of 2 mm and has, at its end, a wire mesh having openings of 150 micrometers and a diameter of 25 mm is inserted into the filtration cylindrical tube such that the wire mesh comes into contact with the measurement sample, and further a weight is placed such that a load of 2.0 KPa is applied to the measurement sample. In this state, the filtration cylindrical tube is allowed to stand for 1 minute. Then, the cock is opened to allow the solution to flow out, and the time ($T_1$) (seconds) taken until the solution level within the filtration cylindrical tube reaches a 40-mL scale mark from a 60-mL scale mark (i.e., 20 mL of the solution passes) is measured. A liquid-passing speed under a load of 2.0 KPa is calculated from the following equation using the measured time $T_1$ (seconds). It is noted that in the equation, $T_0$ (seconds) is a measured value of a time taken for 20 mL of a saline to pass through the wire mesh in a state where no measurement sample was put in the filtration cylindrical tube.

Liquid-passing speed under load (seconds)=($T_1$–$T_0$)

<<Synthesis of Water-Absorbent Resin Powder>>

Synthesis Example 1

155 parts by mass (2.15 parts by mol) of a water-soluble ethylenically unsaturated monomer (a1) {acrylic acid, manufactured by Mitsubishi Chemical Corporation, purity: 100%}, 0.519 parts by mass (0.002 parts by mol) of an internal crosslinking agent (b1) {pentaerythritol triallyl ether, manufactured by Daiso Co., Ltd.}, and 340.27 parts by mass of deionized water were kept at 1 degree centigrade while being stirred and mixed. After nitrogen was introduced into the mixture to reduce a dissolved oxygen amount to 0.1 ppm or less, 0.31 parts by mass of a 1% aqueous hydrogen peroxide solution, 1.1625 parts by mass of a 1% aqueous ascorbic acid solution, and 2.325 parts by mass of a 0.5% aqueous 2,2'-azobis [2-methyl-N-(2-hydroxyethyl)-propionamide] solution were added and mixed to initiate polymerization. After the temperature of the mixture reached 85 degrees centigrade, the polymerization was conducted at 85 plus or minus 2 degrees centigrade for about 10 hours, to obtain a water-containing gel (1).

Next, while 502.27 parts by mass of the water-containing gel (1) was chopped with a mincing machine (12VR-400K manufactured by KIRE ROYAL Co., LTD), 128.42 parts by mass of a 48.5% aqueous sodium hydroxide solution was added and mixed, and further 2.4 parts by mass of a 1% aqueous ethylene glycol glycidyl ether solution was added and mixed, to obtain a chopped gel (2) (longest diameter: 5 mm). Further, the chopped gel (2) was dried with an air-flow band dryer {130 degrees centigrade, wind velocity: 15 m/second} to obtain a dried product. The water content of the dried product was 2.1 mass %. The dried product was pulverized with a juicer-mixer (OSTERIZER BLENDER manufactured by Oster Co.), and then the particle size thereof was adjusted to 150 micrometers to 710 micrometers using sieves having openings of 150 micrometers and 710 micrometers, to obtain a dried product particle.

While 100 parts by mass of the dried product particle was stirred at a high-speed (with a high-speed stirring turbulizer manufactured by Hosokawa Micron Corporation; rotational speed: 2000 rpm), 5 parts by mass of a 2% water/methanol mixed solution (mass ratio of water/methanol=70/30) of ethylene glycol diglycidyl ether was added by spraying and mixed, and the mixture was kept still at 120 degrees centigrade for 60 minutes to achieve surface crosslinking, thereby obtaining a crosslinked polymer (A). To 100 parts by mass of the crosslinked polymer (A), 0.2 part by mass of silica (Aerosil 380 manufactured by Toshin Chemicals Co., Ltd.) and 0.01 part by mass of a carboxy-modified polysiloxane (X-22-3701E manufactured by Shin-Etsu Chemical Co., Ltd.) (B3) were added as a surface modifier (B), followed by stirring at 85 degrees centigrade for 60 minutes. The weight average particle size of the obtained resin powder was adjusted to 500 micrometers to obtain a water-absorbent resin powder 1.

Comparative Synthetic Example 1

A comparative water-absorbent resin powder 1 was obtained in the same manner as in Synthetic Example 1, except that "the chopped gel (2) was dried with an air-flow band dryer {130 degrees centigrade, wind velocity: 15 m/second}" was changed to "the chopped gel (2) was dried with an air-flow band dryer {150 degrees centigrade, wind velocity: 5 m/second} (water content of the dried product: 2.2 mass %)".

The properties of the water absorbent resin powder 1 and the comparative water absorbent resin powder 1 are shown in the following Table 1.

Preparation of Adsorbent

As adsorbents, those described in the following were prepared.

Hydrophobized adsorbent 1: Hydrophobized silica ("Aerosil R812" produced by Nippon Aerosil Co., Ltd., having a volume average particle diameter of 7 nm, specific surface area of 260 plus-or-minus 30 $m^2/g$, and surface-treated with a trimethylsilyl group).

Hydrophobized adsorbent 2: Hydrophobized activated carbon (having a volume average particle diameter of 1.4 mm, a specific surface area of 1100 $m^2/g$, and surface-treated with dimethyldichlorosilane).

Comparative adsorbent 1: Hydrophilic silica ("Aerosil 380" produced by Nippon Aerosil Co., Ltd.).

Comparative adsorbent 2: Hydrophilic activated carbon ("Kuraray coal (Registered trademark) GG10/20" produced by Kuraray Chemical Co., Ltd.).

The hydrophobized adsorbent 2 (hydrophobized activated carbon) was produced with the method described below.

In order to remove moisture from the hydrophobized activated carbon, as a pre-treatment, 500 g of Kuraray coal GG10/20 (produced by Kuraray Chemical Co., Ltd.) was vacuum dried for 3 hours at 160 degrees centigrade. Next, 0.02 g of dimethyldichlorosilane which is a silane coupling agent was dripped into ethanol that had been dehydrated in a glow box (temperature: about 22 degrees centigrade, humidity: equal to or lower than 20%) atmosphere, and the pre-treated activated carbon was inserted therein and was left still for 24 hours or longer. Then the mixture was filtered, and vacuum dried at 100 degrees centigrade for 4 hours to produce the hydrophobized adsorbent 2 which is a hydrophobized activated carbon.

Absorbent Article Manufacturing

Absorbent Article 1

A synthetic-rubber based hot melt adhesive was applied on an air-through nonwoven fabric as a nonwoven fabric, and the hydrophobized adsorbent 1 (hydrophobized silica) was sprayed thereon in streaks to manufacture an adsorption sheet. The adsorption sheet had a dimension of 10 cm×40 cm, and a hydrophobized adsorbent amount of 0.5 g per sheet.

Next, an absorbent article (disposable diaper) 1 was manufactured by arranging, sequentially from the top, a liquid permeable air-through nonwoven fabric, a tissue paper, the adsorption sheet, an absorption layer obtained by mixing the water absorbent resin powder 1 and pulp, and a liquid impermeable back sheet (50 mass % of polyethylene, 50 mass % of calcium carbonate). The absorption layer had a dimension of 10 cm×40 cm, a water absorbent resin powder amount of 10 g per sheet, and a pulp amount of 10 g per sheet.

TABLE 1

| | Properties of Water Absorbent Resin Powder | | | | | | |
|---|---|---|---|---|---|---|---|
| | Bulk density (g/ml) | Absorption speed (seconds) | Absorption speed under load (seconds) | Moisture absorption blocking rate (%) | Absorption ratio (g/g) | Water retention amount (g/g) | Weight average particle diameter (micro-meter) |
| Water absorbent resin powder 1 | 0.71 | 58 | 15 | 1 | 60 | 35 | 500 |
| Comparative water-absorbent resin powder 1 | 0.78 | 65 | 18 | 1 | 60 | 36 | 500 |

In the obtained absorbent article, the content of the hydrophobized adsorbent was 5 parts by mass with respect to 100 parts by mass of the water absorbent resin powder.

Absorbent Article 2

An absorbent article 2 was manufactured in a manner similar to that for the absorbent article 1, except for changing "hydrophobized adsorbent 1" to "hydrophobized adsorbent 2 (hydrophobized activated carbon)."

Comparative Absorbent Article 1

A comparative absorbent article 1 was manufactured in a manner similar to that for the absorbent article 1, except for changing "hydrophobized adsorbent 1" to "comparative adsorbent 1 (hydrophilic silica)."

Comparative Absorbent Article 2

A comparative absorbent article 2 was manufactured in a manner similar to that for the absorbent article 1, except for changing "hydrophobized adsorbent 1" to "comparative adsorbent 2 (hydrophilic activated carbon)."

Absorbent Article 3

An absorbent article 3 was manufactured by arranging, sequentially from the top, a liquid permeable air-through nonwoven fabric, a tissue paper, an absorption layer obtained by mixing a water absorbent resin, pulp, and the hydrophobized adsorbent 2, and a liquid impermeable back sheet (50 mass % of polyethylene, 50 mass % of calcium carbonate). The absorption layer had a dimension of 10 cm×40 cm, a water absorbent resin powder amount of 10 g per sheet, and a pulp amount of 10 g per sheet.

In the obtained absorbent article, the content of the hydrophobized adsorbent was 5 parts by mass with respect to 100 parts by mass of the water absorbent resin powder.

Comparative Absorbent Article 3

A comparative absorbent article 3 was manufactured in a manner similar to that for the absorbent article 3, except for changing "hydrophobized adsorbent 2" to "comparative adsorbent 2."

Absorbent Article 4

An absorbent article 4 was manufactured by arranging, sequentially from the top, a liquid permeable air-through nonwoven fabric, a tissue paper, an absorption layer obtained by disposing the hydrophobized adsorbent 2 on an absorption layer obtained by mixing a water absorbent resin and pulp, and a liquid impermeable back sheet (50 mass % of polyethylene, 50 mass % of calcium carbonate). The absorption layer had a dimension of 10 cm×40 cm, a water absorbent resin powder amount of 10 g per sheet, a pulp amount of 10 g per sheet, and a hydrophobized adsorbent amount of 0.5 g per sheet.

In the obtained absorbent article, the content of the hydrophobized adsorbent was 5 parts by mass with respect to 100 parts by mass of the water absorbent resin powder.

Comparative Absorbent Article 4

A comparative absorbent article 4 was manufactured in a manner similar to that for the absorbent article 4, except for changing "hydrophobized adsorbent 2" to "comparative adsorbent 2."

Comparative Absorbent Article 5

A comparative absorbent article 5 was manufactured in a manner similar to that for the absorbent article 1, except for changing "water absorbent resin powder 1" to "comparative water-absorbent resin powder 1."

The manufactured absorbent articles were human-tested and their absorption speeds were evaluated, and the results are shown in Table 2. It should be noted that methods for each evaluation were conducted as described below.

(Human-Testing of Absorbent Articles)

Description regarding human-testing of the absorbent articles will be provided with reference to FIG. 9. FIG. 9 is a schematic diagram showing a sealed state of an absorbent article for the human-testing of the absorbent article. The absorbent body 2 of the absorbent article (disposable diaper) 1 was caused to absorb 450 mL of a saline solution 80. In order to allow vapor to pass through the back sheet and escape outside, the absorbent article 1 was folded in two and the end portion of the back sheet was sealed with a tape 81. After keeping the absorbent article for 3 hours in a 40 degrees centigrade environment, sensory evaluation of the dryness of the surface (surface of the back sheet) of the absorbent article was conducted. 30 adult testers were asked to touch the surface of the absorbent article, and were asked to evaluate the degree of wetness perception of the surface with a 5-scale grade of 1 to 5 shown below. An average value of the grades obtained from the 30 testers was used as an evaluation result.

<Grades>

1: Dry.
2: It is slightly damp but dry.
3: Feels slightly damp.
4: Feels damp.
5: Damp enough to wet hands.

(Absorption Rate)

150 mL of saline solutions were absorbed by the absorbent articles. During the pouring, the speed was measured from the start of the pour until liquid disappeared from the surface, and the speed was classified by the following evaluation standard.

<Classification>

Poor: 20 seconds or longer.
Fair: longer than 10 seconds and shorter than 20 seconds.
Good: 10 seconds or shorter.

TABLE 2

|  | Absorbent article | Adsorbent | Water absorbent resin powder | Human testing (grade) | Absorption rate (grade) |
| --- | --- | --- | --- | --- | --- |
| Example 1 | Absorbent article 1 | Hydrophobized silica | Water absorbent resin powder 1 | 2.9 | Good |
| Example 2 | Absorbent article 2 | Hydrophobized activated carbon | Water absorbent resin powder 1 | 2.2 | Good |
| Example 3 | Absorbent article 3 | Hydrophobized activated carbon | Water absorbent resin powder 1 | 2.8 | Good |
| Example 4 | Absorbent article 4 | Hydrophobized activated carbon | Water absorbent resin powder 1 | 2.5 | Good |
| Comparative Example 1 | Comparative absorbent article 1 | Hydrophilized silica | Water absorbent resin powder 1 | 4.4 | Good |
| Comparative Example 2 | Comparative absorbent article 2 | Hydrophilized activated carbon | Water absorbent resin powder 1 | 4.0 | Fair |

TABLE 2-continued

| | Absorbent article | Adsorbent | Water absorbent resin powder | Human testing (grade) | Absorption rate (grade) |
|---|---|---|---|---|---|
| Comparative Example 3 | Comparative absorbent article 3 | Hydrophilized activated carbon | Water absorbent resin powder 1 | 4.3 | Good |
| Comparative Example 4 | Comparative absorbent article 4 | Hydrophilized activated carbon | Water absorbent resin powder 1 | 4.1 | Good |
| Comparative Example 5 | Comparative absorbent article 5 | Hydrophobized silica | Comparative Water absorbent resin powder 1 | 3.5 | Poor |

As can be understood from Table 2, the absorbent articles in Examples 1 to 4 show excellent dryness and absorption speeds when compared to the comparative absorbent articles of Comparative Examples 1 to 5. This is because the absorbent articles include the hydrophobized adsorbent and the water absorbent resin powder having an absorption speed in a range from 6 seconds to 60 seconds determined by the vortex method, and thus the water absorbent resin powder immediately absorbs body fluid before the hydrophobized adsorbent absorbs the body fluid. Therefore, since water vapor adsorption performance of the hydrophobized adsorbent does not deteriorate, it is thought that fine dryness and fine absorption speed are obtained.

On the other hand, the comparative absorbent articles of Comparative Examples 1 to 5 had inferior results when compared to the absorbent articles of Examples 1 to 4. Since the adsorbents included in Comparative Examples 1 to 4 have low hydrophobicity (i.e., hydrophilic), when body fluid such as urine is excreted, the adsorbents absorb the body fluid before adsorbing water vapor and thus hardly function as an adsorbent for adsorbing water vapor. Accordingly, it is estimated that this is the reason an inferior result regarding dryness was obtained from the evaluation by human.

The present invention includes the following embodiments.

Embodiment 1

An absorbent article comprising:
an absorbent body composed of at least one absorption layer, wherein the absorbent body includes a hydrophobized adsorbent and (a) a water absorbent resin powder having an absorption speed in a range from 6 seconds to 60 seconds determined by a vortex method.

Embodiment 2

The absorbent article according to embodiment 1, wherein the hydrophobized adsorbent is at least one selected from the group consisting of hydrophobized silica, hydrophobized alumina, hydrophobized zeolite, and hydrophobized activated carbon.

Embodiment 3

The absorbent article according to embodiment 1 or 2, wherein the water absorbent resin powder satisfies the following requirements of (b) to (d).

(b) Moisture absorption blocking rate: 10% or lower
(c) Absorption ratio: 30 g/g to 70 g/g
(d) Water retention amount: 25 g/g to 65 g/g Embodiment 4

The absorbent article according to any one of embodiments 1 to 3, wherein the absorbent body includes the hydrophobized adsorbent in an amount from 0.01 part by mass to 20 parts by mass with respect to 100 parts by mass of the water absorbent resin powder.

Embodiment 5

The absorbent article according to any one of embodiments 1 to 4, wherein the absorbent body includes the hydrophobized adsorbent on a skin surface side thereof.

Embodiment 6

The absorbent article according to any one of embodiments 1 to 5, comprising a surface sheet material disposed on a skin surface side of the absorbent body and a liquid impermeable exterior sheet material disposed on an external surface side of the absorbent body, wherein at least one part of the surface sheet material is liquid permeable.

Embodiment 7

The absorbent article according to any one of embodiments 1 to 6, wherein the absorbent article is an open-type or pants-type disposable diaper.

INDUSTRIAL APPLICABILITY

The present invention can be suitably used, for example, for absorbent articles which absorb the fluid excreted from human body, in particular used for absorbent articles such as disposable diapers, sanitary napkins, incontinence pads, and breast-milk pads.

REFERENCE SIGNS LIST

1: disposable diaper (absorbent article), 2: absorbent body, 3: front abdominal portion, 4: hydrophobized adsorbent, 5: back portion, 6: water-absorbent resin powder having an absorption speed in a range from 6 seconds to 60 seconds determined by a vortex method, 7: crotch portion, 8: fibrous base material, 9: notch, 10: liquid permeable nonwoven sheet, 11: exterior sheet material, 12: end edge, 13: absorbent main body, 15: front-side waist elastic member, 17 back-side waist elastic member, 19: front-side leg elastic member, 21: back-side leg elastic member, 23: front-side torso circumference elastic member, 25: back-side torso circumference elastic member, 27: liquid permeable top sheet, 29: liquid impermeable back sheet, 31: front-side end holding sheet, 33: back-side end holding sheet, 34: joining part, 35: side sheet, 37: elastic member, 80: saline solution, 81: tape

The invention claimed is:

1. An absorbent article comprising:
an absorbent body composed of at least one absorption layer,
wherein the absorbent body includes a hydrophobized adsorbent and a water absorbent resin powder having (a) an absorption speed in a range from 6 seconds to 60 seconds determined by a vortex method, and
wherein the hydrophobized adsorbent is provided on a skin surface side of the absorbent body, relative to the water absorbent resin powder having (a) the absorption speed in the range of from 6 seconds to 60 seconds determined by the vortex method,
wherein the hydrophobized adsorbent is hydrophobized silica having an volume average particle diameter of 2 to 16 nm.

2. The absorbent article according to claim 1, wherein the water absorbent resin powder satisfies the following requirements of (b) to (d):
(b) Moisture absorption blocking rate: 10% or lower;
(c) Absorption ratio: 30 g/g to 70 g/g; and
(d) Water retention amount: 25 g/g to 65 g/g.

3. The absorbent article according to claim 1, wherein the absorbent body includes the hydrophobized adsorbent in an amount from 0.01 part by mass to 20 parts by mass with respect to 100 parts by mass of the water absorbent resin powder.

4. The absorbent article according to claim 1, comprising a surface sheet material disposed on a skin surface side of the absorbent body and a liquid impermeable exterior sheet material disposed on an external surface side of the absorbent body, wherein at least one part of the surface sheet material is liquid permeable.

5. The absorbent article according to claim 1, wherein the absorbent article is an open-type or pants-type disposable diaper.

6. The absorbent article according to claim 1, wherein the hydrophobized adsorbent is provided on the skin surface side of the absorbent body, relative to a water absorbent material comprising the water absorbent resin powder having (a) the absorption speed in the range from 6 seconds to 60 seconds determined by the vortex method.

7. The absorbent article according to claim 6, wherein the hydrophobized adsorbent is disposed inside the at least one absorption layer including the water absorbent resin powder having (a) the absorption speed in the range from 6 seconds to 60 seconds determined by the vortex method as the water absorbent material.

8. The absorbent article according to claim 7, wherein the absorbent body is composed of two or more absorption layers, and the hydrophobized adsorbent is disposed inside the absorption layer located closest to the skin surface side.

9. The absorbent article according to claim 6,
wherein the hydrophobized adsorbent is disposed outside the at least one absorption layer including the water absorbent resin powder having (a) the absorption speed in the range from 6 seconds to 60 seconds determined by the vortex method as the water absorbent material, and
wherein the hydrophobized adsorbent is directly attached to the surface of the absorption layer.

10. The absorbent article according to claim 9,
wherein the absorbent body is composed of two or more absorption layers, and
wherein the hydrophobized adsorbent is directly attached to the surface of the absorption layer located closest to the skin surface side.

11. The absorbent article according to claim 6, wherein an adsorption sheet formed by having the hydrophobized adsorbent attached on a liquid permeable nonwoven fabric sheet is laminated on the at least one absorption layer, the at least one absorption layer including the water absorbent resin powder having (a) the absorption speed in the range from 6 seconds to 60 seconds determined by the vortex method as the water absorbent material.

12. The absorbent article according to claim 11,
wherein the absorbent body is composed of two or more absorption layers, and
wherein the adsorption sheet is laminated on the absorption layer located closest to the skin surface side.

13. The absorbent article according to claim 1, wherein the absorbent body includes the hydrophobized adsorbent in an amount from 5 parts by mass to 20 parts by mass with respect to 100 parts by mass of the water absorbent resin powder.

14. An absorbent article comprising:
an absorbent body composed of at least one absorption layer,
wherein the absorbent body includes a hydrophobized adsorbent and a water absorbent resin powder having (a) an absorption speed in a range from 6 seconds to 60 seconds determined by a vortex method, and
wherein the hydrophobized adsorbent is provided on a skin surface side of the absorbent body, relative to the water absorbent resin powder having (a) the absorption speed in the range of from 6 seconds to 60 seconds determined by the vortex method,
wherein the hydrophobized adsorbent and the water absorbent resin powder having (a) the absorption speed in the range of from 6 seconds to 60 seconds determined by the vortex method are separate from each other.

* * * * *